United States Patent [19]
Harris et al.

[11] Patent Number: 5,932,462
[45] Date of Patent: Aug. 3, 1999

[54] MULTIARMED, MONOFUNCTIONAL, POLYMER FOR COUPLING TO MOLECULES AND SURFACES

[75] Inventors: J. Milton Harris, Huntsville, Ala.; Francesco Maria Veronese, Padua, Italy; Paolo Caliceti, Padua, Italy; Oddone Schiavon, Padua, Italy

[73] Assignee: Shearwater Polymers, Inc., Huntsville, Ala.

[21] Appl. No.: 08/443,383

[22] Filed: May 17, 1995

Related U.S. Application Data

[63] Continuation-in-part of application No. 08/371,065, Jan. 10, 1995, abandoned.
[51] Int. Cl.$^6$ ............................ C12N 9/96; C12N 11/06; C07K 17/00; A01N 63/00
[52] U.S. Cl. ................ 435/188; 424/94.3; 435/177; 435/180; 435/181; 525/54.1; 514/2; 530/402
[58] Field of Search .................. 435/174, 177, 435/180, 181, 188; 424/94.3; 514/2; 525/54.1; 530/402

[56] References Cited

U.S. PATENT DOCUMENTS

| | | | |
|---|---|---|---|
| 4,179,337 | 12/1979 | Davis et al. | 435/181 |
| 4,722,906 | 2/1988 | Guire | 436/501 |
| 5,168,057 | 12/1992 | Oh et al. | 435/174 |
| 5,438,040 | 8/1995 | Ekuiuribe | 514/3 |
| 5,643,575 | 7/1997 | Martinez et al. | 424/194.1 |

FOREIGN PATENT DOCUMENTS

| | | |
|---|---|---|
| 0 473 084 A2 | of 0000 | European Pat. Off. . |
| 0 400 472 A3 | 12/1990 | European Pat. Off. . |
| 0 400 486 A3 | 12/1990 | European Pat. Off. . |
| 0 632 082 A1 | 1/1995 | European Pat. Off. . |
| WO 95/11924 | 5/1995 | WIPO . |

OTHER PUBLICATIONS

H. Wada et al., Antitumor Enzyme: Polyethylene Glycol–modified Asparaginase, *Acad. Sci.* 613, pp. 95–108 (Dec., 1990).

I. Fuke et al., "Synthesis of poly(ethylene glycol) derivatives with different branchings and their use for protein modification," *Journal of Controlled Release* 30 pp. 27–34 (1994).

*Agri. Biol. Chem.*, 52 (8) (1988) pp. 2125–2127, Yamasaki et al: "Novel Polyethylene Glycol Derivatives for Modification of Proteins".

*Bioconjugate Chemistry*, vol. 06, No. 01, Jan., 1995, Washington, D.C., pp. 62–69, XP002004192, Monfardini C. et al: "A Branched Monomethoxypolyethyleneglycol for Protein Modifications".

*Primary Examiner*—David M. Naff
*Attorney, Agent, or Firm*—Bell Seltzer Intellectual Property Law Group of Alston & Bird LLP

[57] ABSTRACT

Multi-armed, monofunctional, and hydrolytically stable polymers are described having the structure

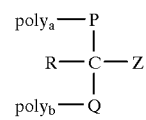

wherein Z is a moiety that can be activated for attachment to biologically active molecules such as proteins and wherein P and Q represent linkage fragments that join polymer arms poly$_a$ and poly$_b$, respectively, to central carbon atom, C, by hydrolytically stable linkages in the absence of aromatic rings and ester groups in the linkage fragments. R typically is hydrogen or methyl, but can be a linkage fragment that includes another polymer arm. A specific example is an mPEG disubstituted lysine having the structure

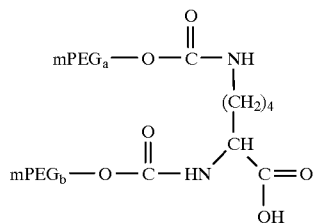

where mPEG$_a$ and mPEG$_b$ have the structure CH$_3$O—(CH$_2$CH$_2$O)$_n$CH$_2$CH$_2$— wherein n may be the same or different for mPEG$_a$ and mPEG$_b$ and can be from 1 to about 1,150 to provide molecular weights of from about 100 to 100,000. The mPEG disubstituted lysine can be purified from a reaction mixture by chromatography in water, including gel filtration chromatography and ion exchange chromatography because the carboxyl group is ionizable. Impurities are removed, including unreacted mPEG and mPEG monosubstituted lysine, to provide the polymer in pure form. Ion exchange chromatography permits fractionation of a greater amount of polymer per run.

49 Claims, 8 Drawing Sheets

- — CATALASE
- ○ — LINEAR mPEG-CATALASE
- □ — CATALASE MODIFIED WITH TWO-ARMED mPEG

- — CATALASE
- ○ — LINEAR mPEG-CATALASE
- □ — CATALASE MODIFIED WITH TWO-ARMED mPEG

MULTIARMED, MONOFUNCTIONAL, POLYMER FOR COUPLING TO MOLECULES AND SURFACES

This application is a continuation-in-part and claims the benefit of the filing date of U.S. Ser. No. 08/371,065, filed Jan. 10, 1995, now abandoned.

FIELD OF THE INVENTION

This invention relates to monofunctional derivatives of poly(ethylene glycol) and related polymers and to methods for their synthesis and activation for use in modifying the characteristics of surfaces and molecules.

BACKGROUND OF THE INVENTION

Improved chemical and genetic methods have made many enzymes, proteins, and other peptides and polypeptides available for use as drugs or biocatalysts having specific catalytic activity. However, limitations exist to use of these compounds.

For example, enzymes that exhibit specific biocatalytic activity sometimes are less useful than they otherwise might be because of problems of low stability and solubility in organic solvents. During in vivo use, many proteins are cleared from circulation too rapidly. Some proteins have less water solubility than is optimal for a therapeutic agent that circulates through the bloodstream. Some proteins give rise to immunological problems when used as therapeutic agents. Immunological problems have been reported from manufactured proteins even where the compound apparently has the same basic structure as the homologous natural product. Numerous impediments to the successful use of enzymes and proteins as drugs and biocatalysts have been encountered.

One approach to the problems that have arisen in the use of polypeptides as drugs or biocatalysts has been to link suitable hydrophilic or amphiphilic polymer derivatives to the polypeptide to create a polymer cloud surrounding the polypeptide. If the polymer derivative is soluble and stable in organic solvents, then enzyme conjugates with the polymer may acquire that solubility and stability. Biocatalysis can be extended to organic media with enzyme and polymer combinations that are soluble and stable in organic solvents.

For in vivo use, the polymer cloud can help to protect the compound from chemical attack, to limit adverse side effects of the compound when injected into the body, and to increase the size of the compound, potentially to render useful compounds that have some medicinal benefit, but otherwise are not useful or are even harmful to an organism. For example, the polymer cloud surrounding a protein can reduce the rate of renal excretion and immunological complications and can increase resistance of the protein to proteolytic breakdown into simpler, inactive substances.

However, despite the benefits of modifying polypeptides with polymer derivatives, additional problems have arisen. These problems typically arise in the linkage of the polymer to the polypeptide. The linkage may be difficult to form. Bifunctional or multifunctional polymer derivatives tend to cross link proteins, which can result in a loss of solubility in water, making a polymer-modified protein unsuitable for circulating through the blood stream of a living organism. Other polymer derivatives form hydrolytically unstable linkages that are quickly destroyed on injection into the blood stream. Some linking moieties are toxic. Some linkages reduce the activity of the protein or enzyme, thereby rendering the protein or enzyme less effective.

The structure of the protein or enzyme dictates the location of reactive sites that form the loci for linkage with polymers. Proteins are built of various sequences of alpha-amino acids, which have the general structure

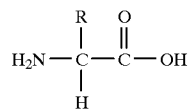

The alpha amino moiety ($H_2N$—) of one amino acid joins to the carboxyl moiety (—COOH) of an adjacent amino acid to form amide linkages, which can be represented as

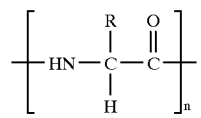

where n can be hundreds or thousands. The terminal amino acid of a protein molecule contains a free alpha amino moiety that is reactive and to which a polymer can be attached. The fragment represented by R can contain reactive sites for protein biological activity and for attachment of polymer.

For example, in lysine, which is an amino acid forming part of the backbone of most proteins, a reactive amino (—$NH_2$) moiety is present in the epsilon position as well as in the alpha position. The epsilon —$NH_2$ is free for reaction under conditions of basic pH. Much of the art has been directed to developing polymer derivatives having active moieties for attachment to the epsilon —$NH_2$ moiety of the lysine fraction of a protein. These polymer derivatives all have in common that the lysine amino acid fraction of the protein typically is modified by polymer attachment, which can be a drawback where lysine is important to protein activity.

Poly(ethylene glycol), which is commonly referred to simply as "PEG," has been the nonpeptidic polymer most used so far for attachment to proteins. The PEG molecule typically is linear and can be represented structurally as

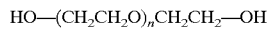

or, more simply, as HO—PEG—OH. As shown, the PEG molecule is difunctional, and is sometimes referred to as "PEG diol." The terminal portions of the PEG molecule are relatively nonreactive hydroxyl moieties, —OH, that can be activated, or converted to functional moieties, for attachment of the PEG to other compounds at reactive sites on the compound.

For example, the terminal moieties of PEG diol have been functionalized as active carbonate ester for selective reaction with amino moieties by substitution of the relatively non-reactive hydroxyl moieties, —OH, with succinimidyl active ester moieties from N-hydroxy succinimide. The succinimidyl ester moiety can be represented structurally as

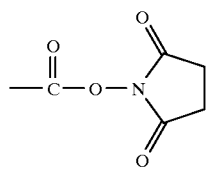

Difunctional PEG, functionalized as the succinimidyl carbonate, has a structure that can be represented as

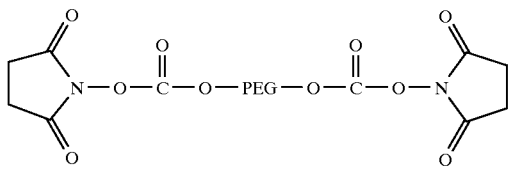

Difunctional succinimidyl carbonate PEG has been reacted with free lysine monomer to make high molecular weight polymers. Free lysine monomer, which is also known as alpha, epsilon diaminocaproic acid, has a structure with reactive alpha and epsilon amino moieties that can be represented as

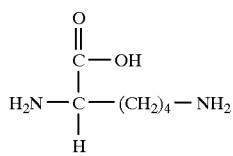

These high molecular weight polymers from difunctional PEG and free lysine monomer have multiple, pendant reactive carboxyl groups extending as branches from the polymer backbone that can be represented structurally as

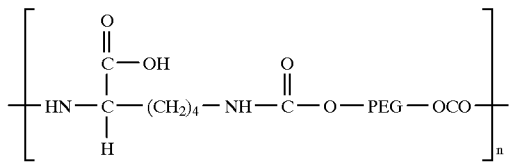

The pendant carboxyl groups typically have been used to couple nonprotein pharmaceutical agents to the polymer. Protein pharmaceutical agents would tend to be cross linked by the multifunctional polymer with loss of protein activity.

Multiarmed PEGs having a reactive terminal moiety on each branch have been prepared by the polymerization of ethylene oxide onto multiple hydroxyl groups of polyols including glycerol. Coupling of this type of multifunctional, branched PEG to a protein normally produces a cross-linked product with considerable loss of protein activity.

It is desirable for many applications to cap the PEG molecule on one end with an essentially nonreactive end moiety so that the PEG molecule is monofunctional. Monofunctional PEGs are usually preferred for protein modification to avoid cross linking and loss of activity. One hydroxyl moiety on the terminus of the PEG diol molecule typically is substituted with a nonreactive methyl end moiety, $CH_3$—. The opposite terminus typically is converted to a reactive end moiety that can be activated for attachment at a reactive site on a surface or a molecule such as a protein.

PEG molecules having a methyl end moiety are sometimes referred to as monomethoxy-poly(ethylene glycol) and are sometimes referred to simply as "mPEG." The mPEG polymer derivatives can be represented structurally as

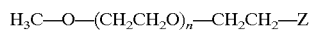

where n typically equals from about 45 to 115 and —Z is a functional moiety that is active for selective attachment to a reactive site on a molecule or surface or is a reactive moiety that can be converted to a functional moiety.

Typically, mPEG polymers are linear polymers of molecular weight in the range of from about 1,000 to 5,000. Higher molecular weights have also been examined, up to a molecular weight of about 25,000, but these mPEGs typically are not of high purity and have not normally been useful in PEG and protein chemistry. In particular, these high molecular weight mPEGs typically contain significant percentages of PEG diol.

Proteins and other molecules typically have a limited number and distinct type of reactive sites available for coupling, such as the epsilon —$NH_2$ moiety of the lysine fraction of a protein. Some of these reactive sites may be responsible for a protein's biological activity. A PEG derivative that attached to a sufficient number of such sites to impart the desired characteristics can adversely affect the activity of the protein, which offsets many of the advantages otherwise to be gained.

Attempts have been made to increase the polymer cloud volume surrounding a protein molecule without further deactivating the protein. Some PEG derivatives have been developed that have a single functional moiety located along the polymer backbone for attachment to another molecule or surface, rather than at the terminus of the polymer. Although these compounds can be considered linear, they are often referred to as "branched" and are distinguished from conventional, linear PEG derivatives since these molecules typically comprise a pair of mPEG- molecules that have been joined by their reactive end moieties to another moiety, which can be represented structurally as —T—, and that includes a reactive moiety, —Z, extending from the polymer backbone. These compounds have a general structure that can be represented as

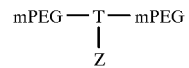

These monofunctional mPEG polymer derivatives show a branched structure when linked to another compound. One such branched form of mPEG with a single active binding site, —Z, has been prepared by substitution of two of the chloride atoms of trichloro-s-triazine with mPEG to make mPEG-disubstituted chlorotriazine. The third chloride is used to bind to protein. An mPEG disubstituted chlorotriazine and its synthesis are disclosed in Wada, H., Imamura, I., Sako, M., Katagiri, S., Tarui, S., Nishimura, H., and Inada, Y. (1990) Antitumor enzymes: polyethylene glycol-modified asparaginase. *Ann. N.Y. Acad. Sci.* 613, 95–108. Synthesis of mPEG disubstituted chlorotriazine is represented structurally below.

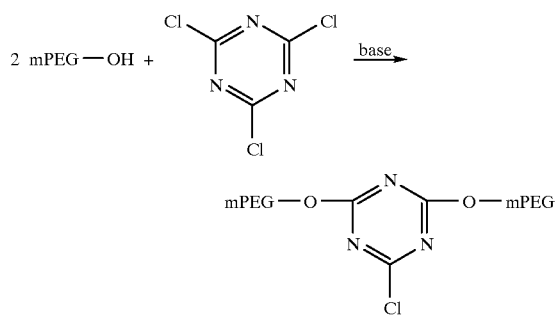

However, mPEG-disubstituted chlorotriazine and the procedure used to prepare it present severe limitations because coupling to protein is highly nonselective. Several types of amino acids other than lysine are attacked and many proteins are inactivated. The intermediate is toxic. Also, the mPEG-disubstituted chlorotriazine molecule reacts with water, thus substantially precluding purification of the branched mPEG structure by commonly used chromatographic techniques in water.

A branched mPEG with a single activation site based on coupling of mPEG to a substituted benzene ring is disclosed in European Patent Application Publication No. 473 084 A2. However, this structure contains a benzene ring that could have toxic effects if the structure is destroyed in a living organism.

Another branched mPEG with a single activation site has been prepared through a complex synthesis in which an active succinate moiety is attached to the mPEG through a weak ester linkage that is susceptible to hydrolysis. An mPEG—OH is reacted with succinic anhydride to make the succinate. The reactive succinate is then activated as the succinimide. The synthesis, starting with the active succinimide, includes the following steps, represented structurally below.

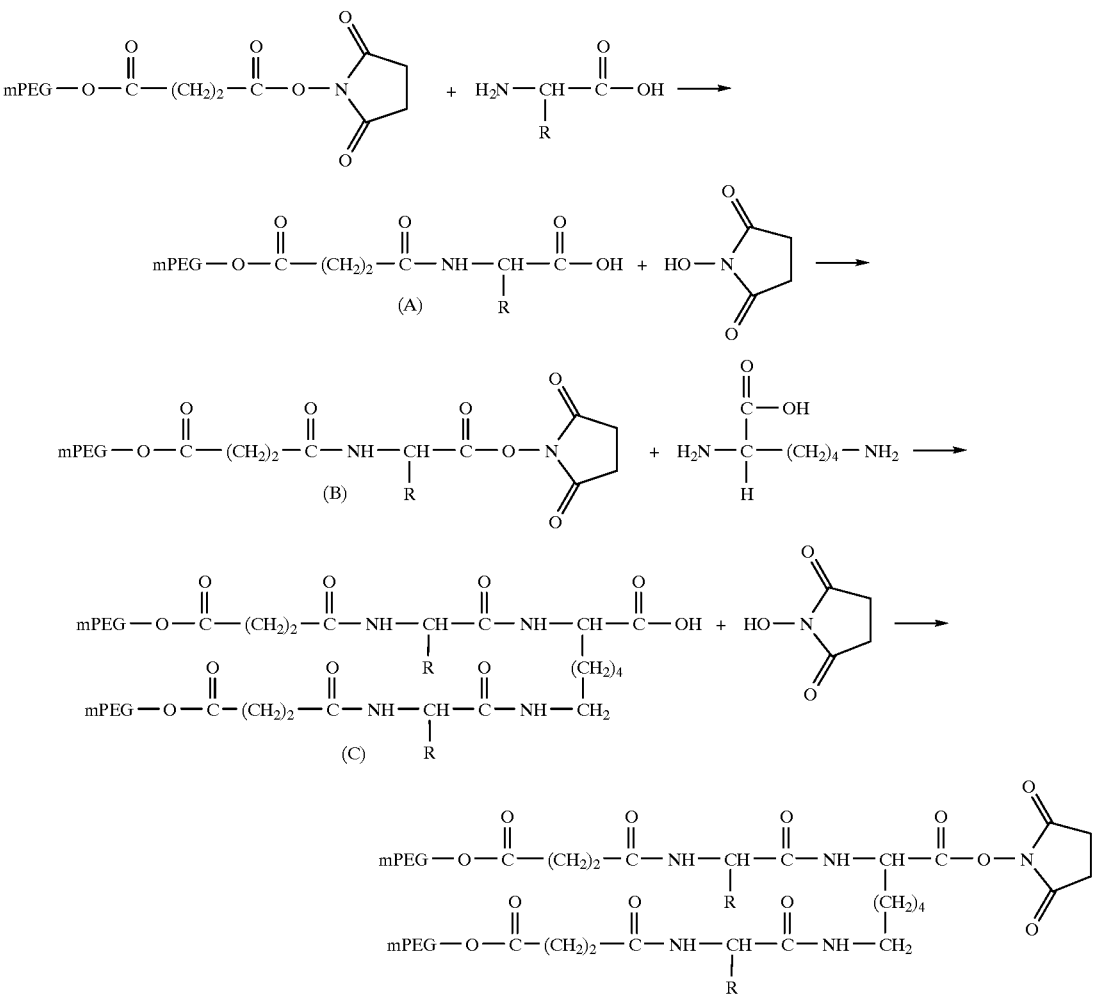

The mPEG activated as the succinimide, mPEG succinimidyl succinate, is reacted in the first step as shown above with norleucine. The symbol —R in the synthesis represents the n-butyl moiety of norleucine. The mPEG and norleucine conjugate (A) is activated as the succinimide in the second step by reaction with N-hydroxy succinimide. As represented in the third step, the mPEG and norleucine conjugate activated as the succinimide (B) is coupled to the alpha and epsilon amino moieties of lysine to create an mPEG disubstituted lysine (C) having a reactive carboxyl moiety. In the fourth step, the mPEG disubstituted lysine is activated as the succinimide.

The ester linkage formed from the reaction of the mPEG—OH and succinic anhydride molecules is a weak linkage that is hydrolytically unstable. In vivo application is therefore limited. Also, purification of the branched mPEG is precluded by commonly used chromatographic techniques in water, which normally would destroy the molecule.

The molecule also has relatively large molecular fragments between the carboxyl group activated as the succinimide and the mPEG moieties due to the number of steps in the synthesis and to the number of compounds used to create the fragments. These molecular fragments are sometimes referred to as "linkers" or "spacer arms," and have the potential to act as antigenic sites promoting the formation of antibodies upon injection and initiating an undesirable immunological response in a living organism.

SUMMARY OF THE INVENTION

The invention provides a branched or "multi-armed" amphiphilic polymer derivative that is monofunctional, hydrolytically stable, can be prepared in a simple, one-step reaction, and possesses no aromatic moieties in the linker fragments forming the linkages with the polymer moieties. The derivative can be prepared without any toxic linkage or potentially toxic fragments. Relatively pure polymer molecules of high molecular weight can be created. The polymer can be purified by chromatography in water. A multi-step method can be used if it is desired to have polymer arms that differ in molecular weight. The polymer arms are capped with relatively nonreactive end groups. The derivative can include a single reactive site that is located along the polymer backbone rather than on the terminal portions of the polymer moieties. The reactive site can be activated for selective reactions.

The multi-armed polymer derivative of the invention having a single reactive site can be used for, among other things, protein modification with a high retention of protein activity. Protein and enzyme activity can be preserved and in some cases is enhanced. The single reactive site can be converted to a functional group for highly selective coupling to proteins, enzymes, and surfaces. A larger, more dense polymer cloud can be created surrounding a biomolecule with fewer attachment points to the biomolecule as compared to conventional polymer derivatives having terminal functional groups. Hydrolytically weak ester linkages can be avoided. Potentially harmful or toxic products of hydrolysis can be avoided. Large linker fragments can be avoided so as to avoid an antigenic response in living organisms. Cross linking is avoided.

The molecules of the invention can be represented structurally as $poly_a$—P—CR(—Q—$poly_b$)—Z or:

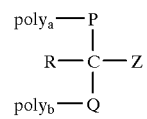

$Poly_a$ and $poly_b$ represent nonpeptidic and substantially nonreactive water soluble polymeric arms that may be the same or different. C represents carbon. P and Q represent linkage fragments that may be the same or different and that join polymer arms $poly_a$ and $poly_b$, respectively, to C by hydrolytically stable linkages in the absence of aromatic rings in the linkage fragments. R is a moiety selected from the group consisting of H, substantially nonreactive, usually alkyl, moieties, and linkage fragments attached by a hydrolytically stable linkage in the absence of aromatic rings to a nonpeptidic and substantially nonreactive water soluble polymeric arm. The moiety —Z comprises a moiety selected from the group consisting of moieties having a single site reactive toward nucleophilic moieties, sites that can be converted to sites reactive toward nucleophilic moieties, and the reaction product of a nucleophilic moiety and moieties having a single site reactive toward nucleophilic moieties.

Typically, the moiety —P—CR(—Q—)—Z is the reaction product of a linker moiety and the reactive site of monofunctional, nonpeptidic polymer derivatives, $poly_a$—W and $poly_b$—W, in which W is the reactive site. Polymer arms $poly_a$ and $poly_b$ are nonpeptidic polymers and can be selected from polymers that have a single reactive moiety that can be activated for hydrolytically stable coupling to a suitable linker moiety. The linker has the general structure X—CR—(Y)—Z, in which X and Y represent fragments that contain reactive sites for coupling to the polymer reactive site W to form linkage fragments P and Q, respectively.

In one embodiment, at least one of the polymer arms is a poly(ethylene glycol) moiety capped with an essentially nonreactive end group, such as a monomethoxy-poly (ethylene glycol) moiety ("mPEG-"), which is capped with a methyl end group, $CH_3$—. The other branch can also be an mPEG moiety of the same or different molecular weight, another poly(ethylene glycol) moiety that is capped with an essentially nonreactive end group other than methyl, or a different nonpeptidic polymer moiety that is capped with a nonreactive end group such as a capped poly(alkylene oxide), a poly(oxyethylated polyol), a poly(olefinic alcohol), or others.

For example, in one embodiment $poly_a$ and $poly_b$ are each monomethoxy-poly(ethylene glycol) ("mPEG") of the same or different molecular weight. The mPEG-disubstituted derivative has the general structure $mPEG_a$—P—CH(—Q—$mPEG_b$)—Z. The moieties $mPEG_a$— and $mPEG_b$— have the structure $CH_3$—$(CH_2CH_2O)_n$$CH_2CH_2$— and n may be the same or different for $mPEG_a$ and $mPEG_b$. Molecules having values of n of from 1 to about 1,150 are contemplated.

The linker fragments P and Q contain hydrolytically stable linkages that may be the same or different depending upon the functional moiety on the mPEG molecules and the molecular structure of the linker moiety used to join the mPEG moieties in the method for synthesizing the multi-armed structure. The linker fragments typically are alkyl fragments containing amino or thiol residues forming a linkage with the residue of the functional moiety of the polymer. Depending on the degree of substitution desired, linker fragments P and Q can include reactive sites for joining additional monofunctional nonpeptidic polymers to the multi-armed structure.

The moiety —R can be a hydrogen atom, H, a nonreactive fragment, or, depending on the degree of substitution desired, R can include reactive sites for joining additional monofunctional nonpeptidic polymers to the multi-armed structure.

The moiety —Z can include a reactive moiety for which the activated nonpeptidic polymers are not selective and that can be subsequently activated for attachment of the derivative to enzymes, other proteins, nucleotides, lipids, liposomes, other molecules, solids, particles, or surfaces. The moiety —Z can include a linkage fragment —$R_z$. Depending on the degree of substitution desired, the $R_z$ fragment can include reactive sites for joining additional monofunctional nonpeptidic polymers to the multi-armed structure.

Typically, the —Z moiety includes terminal functional moieties for providing linkages to reactive sites on proteins, enzymes, nucleotides, lipids, liposomes, and other materials. The moiety —Z is intended to have a broad interpretation and to include the reactive moiety of monofunctional polymer derivatives of the invention, activated derivatives, and conjugates of the derivatives with polypeptides and other substances. The invention includes biologically active conjugates comprising a biomolecule, which is a biologically active molecule, such as a protein or enzyme, linked through an activated moiety to the branched polymer derivative of the invention. The invention includes biomaterials comprising a solid such as a surface or particle linked through an activated moiety to the polymer derivatives of the invention.

In one embodiment, the polymer moiety is an mPEG moiety and the polymer derivative is a two-armed mPEG derivative based upon hydrolytically stable coupling of mPEG to lysine. The mPEG moieties are represented structurally as $CH_3O$—$(CH_2CH_2O)_n CH_2CH_2$— wherein n may be the same or different for poly$_a$— and poly$_b$— and can be from 1 to about 1,150 to provide molecular weights of from about 100 to 100,000. The —R moiety is hydrogen. The —Z moiety is a reactive carboxyl moiety. The molecule is represented structurally as follows:

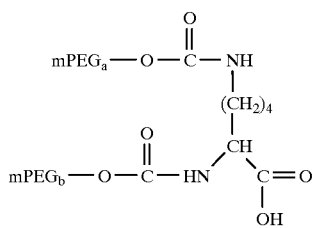

The reactive carboxyl moiety of hydrolytically stable mPEG-disubstituted lysine, which can also be called alpha, epsilon-mPEG lysine, provides a site for interacting with ion exchange chromatography media and thus provides a mechanism for purifying the product. These purifiable, high molecular weight, monofunctional compounds have many uses. For example, mPEG-disubstituted lysine, activated as succinimidyl ester, reacts with amino groups in enzymes under mild aqueous conditions that are compatible with the stability of most enzymes. The mPEG-disubstituted lysine of the invention, activated as the succinimidyl ester, is represented as follows:

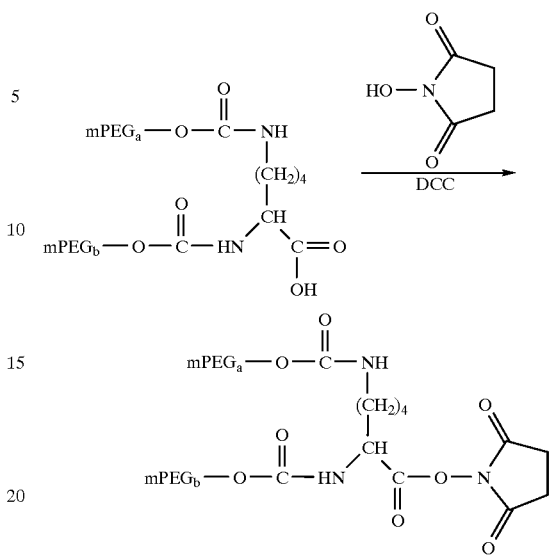

The invention includes methods of synthesizing the polymers of the invention. The methods comprise reacting an active suitable polymer having the structure poly—W with a linker moiety having the structure X—CR—(Y)Z to form poly$_a$—P—CR(—Q—poly$_b$)—Z. The poly moiety in the structure poly—W can be either poly$_a$ or poly$_b$ and is a polymer having a single reactive moiety W. The W moiety is an active moiety that is linked to the polymer moiety directly or through a hydrolytically stable linkage. The moieties X and Y in the structure X—CR—(Y)Z are reactive with W to form the linkage fragments Q and P, respectively. If the moiety R includes reactive sites similar to those of X and Y, then R can also be modified with a poly-W, in which the poly can be the same as or different from poly$_a$ or poly$_b$. The moiety Z normally does not include a site that is reactive with W. However, X, Y, R, and Z can each include one or more such reactive sites for preparing monofunctional polymer derivatives having more than two branches.

The method of the invention typically can be accomplished in one or two steps. The method can include additional steps for preparing the compound poly-W and for converting a reactive Z moiety to a functional group for highly selective reactions.

The active Z moiety includes a reactive moiety that is not reactive with W and can be activated subsequent to formation of poly$_a$—P—CR(—Q—poly$_b$)—Z for highly selective coupling to selected reactive moieties of enzymes and other proteins or surfaces or any molecule having a reactive nucleophilic moiety for which it is desired to modify the characteristics of the molecule.

In additional embodiments, the invention provides a multi-armed mPEG derivative for which preparation is simple and straightforward. Intermediates are water stable and thus can be carefully purified by standard aqueous chromatographic techniques. Chlorotriazine activated groups are avoided and more highly selective functional groups are used for enhanced selectivity of attachment and much less loss of activity upon coupling of the mPEG derivatives of the invention to proteins, enzymes, and other peptides. Large spacer arms between the coupled polymer and protein are avoided to avoid introducing possible antigenic sites. Toxic groups, including triazine, are avoided. The polymer backbone contains no hydrolytically weak ester linkages that could break down during in vivo applications. Monofunctional polymers of double the molecular weight as compared to the individual mPEG moieties can be provided, with mPEG dimer structures having molecular weights of up to at least about 50,000, thus avoiding the common problem of difunctional impurities present in conventional, linear mPEGs.

BRIEF DESCRIPTION OF THE DRAWINGS

FIG. 2(a) is based on data taken after a 15 minute incubation period at the indicated temperatures. FIG. 2(b) is based on data taken over a 20 hour period at different pH values.

DETAILED DESCRIPTION

Figure 1A:
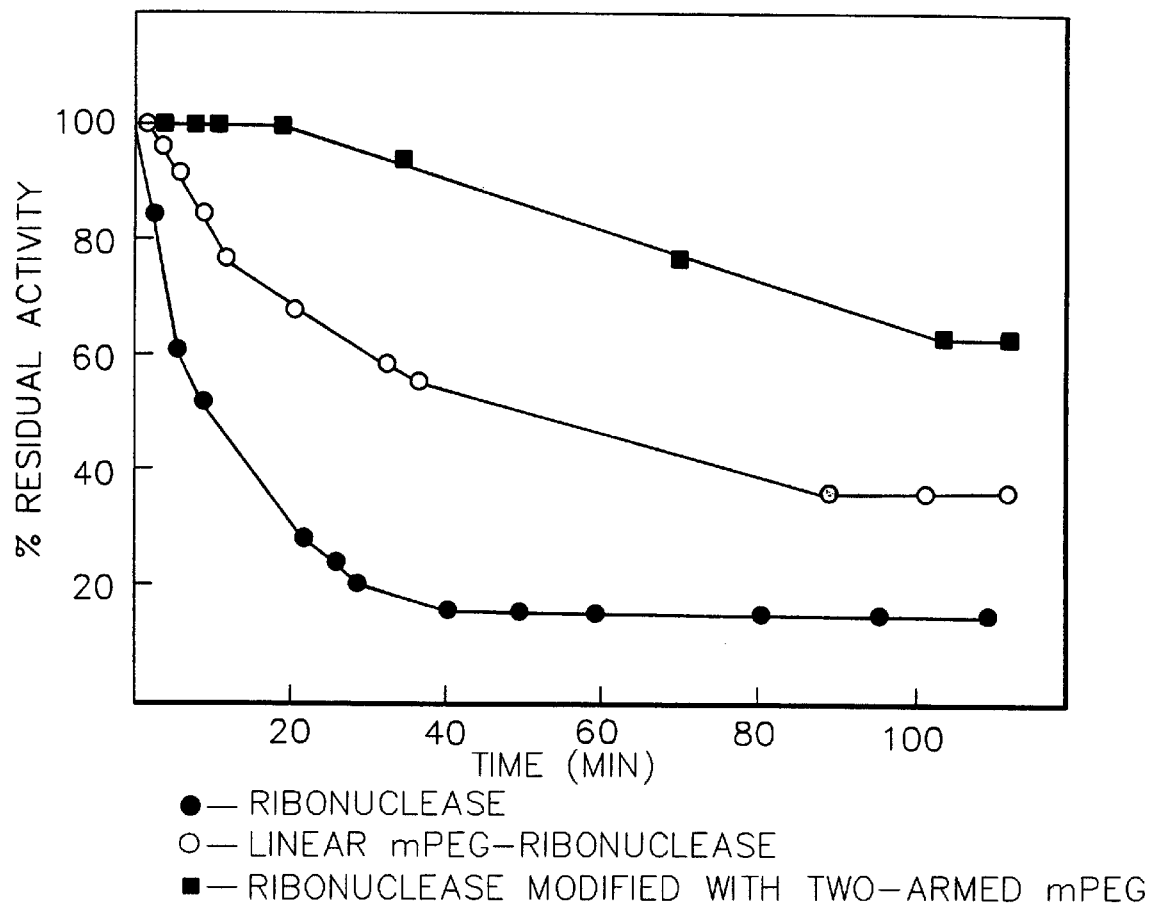
FIGS. 1(a), 1(b), and 1(c) illustrate the time course of digestion of ribonuclease (●), conventional, linear mPEG-modified ribonuclease (○), and ribonuclease modified with a multi-armed mPEG of the invention (■) as assessed by enzyme activity upon incubation with pronase (FIG. 1(a)), elastase (FIG. 1(b)), and subtilisin (FIG. 1(c)).

I. Preparation of a Hydrolytically Stable mPEG-Disubstituted Lysine.

Two procedures are described for the preparation of a hydrolytically stable, two-armed, mPEG-disubstituted lysine. The first procedure is a two step procedure, meaning that the lysine is substituted with each of the two mPEG moieties in separate reaction steps. Monomethoxy-poly (ethylene glycol) arms of different lengths or of the same length can be substituted onto the lysine molecule, if desired, using the two step procedure. The second procedure is a one step procedure in which the lysine molecule is substituted with each of the two mPEG moieties in a single reaction step. The one step procedure is suitable for preparing mPEG-disubstituted lysine having mPEG moieties of the same length.

Unlike prior multisubstituted structures, no aromatic ring is present in the linkage-joining the nonpeptidic polymer arms produced by either the one or two step methods described below that could result in toxicity if the molecule breaks down in vivo. No hydrolytically weak ester linkages are present in the linkage. Lengthy linkage chains that could promote an antigenic response are avoided.

The terms "group," "functional group," "moiety," "active moiety," "reactive site," "radical," and similar terms are somewhat synonymous in the chemical arts and are used in the art and herein to refer to distinct, definable portions or units of a molecule or fragment of a molecule. "Reactive site," "functional group," and "active moiety" refer to units that perform some function or have a chemical activity and are reactive with other molecules or portions of molecules. In this sense a protein or a protein residue can be considered as a molecule and as a functional moiety when coupled to a polymer. A polymer, such as mPEG—COOH has a reactive site, the carboxyl moiety, —COOH, that can be converted to a functional group for selective reactions and attachment to proteins and linker moieties. The converted polymer is said to be activated and to have an active moiety, while the —COOH group is relatively nonreactive in comparison to an active moiety.

The term "nonreactive" is used herein primarily to refer to a moiety that does not readily react chemically with other moieties, such as the methyl alkyl moiety. However, the term "nonreactive" should be understood to exclude carboxyl and hydroxyl moieties, which, although relatively nonreactive, can be converted to functional groups that are of selective reactivity.

The term "biologically active" means a substance, such as a protein, lipid, or nucleotide that has some activity or function in a living organism or in a substance taken from a living organism. For example, an enzyme can catalyze chemical reactions. The term "biomaterial" is somewhat imprecise, and is used herein to refer to a solid material or particle or surface that is compatible with living organisms or tissue or fluids. For example, surfaces that contact blood, whether in vitro or in vivo, can be made nonfouling by attachment of the polymer derivatives of the invention so that proteins do not become attached to the surface.

A. Two Step Procedure

For the two step procedure, an activated mPEG is prepared for coupling to free lysine monomer and then the lysine monomer is disubstituted with the activated mPEG in two steps. The first step occurs in aqueous buffer. The second step occurs in dry methylene chloride. The active moiety of the mPEG for coupling to the lysine monomer can be selected from a number of activating moieties having leaving moieties that are reactive with the amino moieties of lysine monomer. A commercially available activated mPEG, mPEG-p-nitrophenylcarbonate, the preparation of which is discussed below, was used to exemplify the two step procedure.

The two step procedure can be represented structurally as follows:

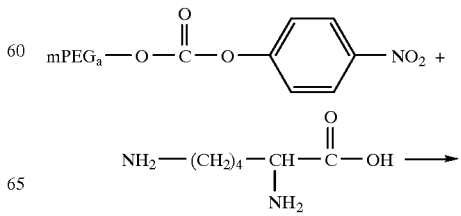

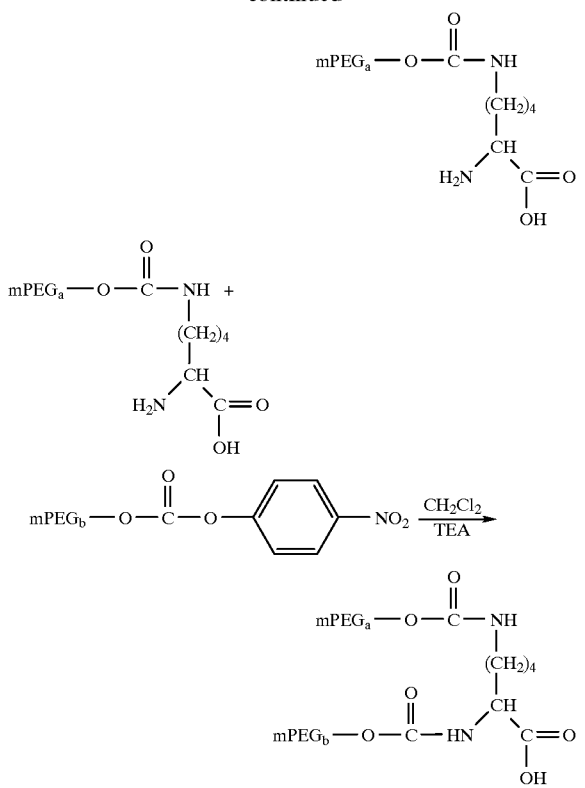

Step 1. Preparation of mPEG-monosubstituted lysine. Modification of a single lysine amino group was accomplished with mPEG-p-nitrophenylcarbonate in aqueous solution where both lysine and mPEG-p-nitrophenylcarbonate are soluble. The mPEG-p-nitrophenylcarbonate has only limited stability in aqueous solution. However, lysine is not soluble in organic solvents in which the activated mPEG is stable. Consequently, only one lysine amino group is modified by this procedure. NMR confirms that the epsilon amino group is modified. Nevertheless, the procedure allows ready chloroform extraction of mPEG-monosubstituted lysine from unreacted lysine and other water soluble by-products, and so the procedure provides a desirable monosubstituted product for disubstitution.

To prepare the mPEG-monosubstituted lysine, 353 milligrams of lysine, which is about 2.5 millimoles, was dissolved in 20 milliliters of water at a pH of about 8.0 to 8.3. Five grams of mPEG-p-nitrophenylcarbonate of molecular weight 5,000, which is about 1 millimole, was added in portions over 3 hours. The pH was maintained at 8.3 with 0.2N NaOH. The reaction mixture was stirred overnight at room temperature. Thereafter, the reaction mixture was cooled to 0° C. and brought to a pH of about 3 with 2N HCl. Impurities were extracted with diethyl ether. The mPEG monosubstituted lysine, having the mPEG substituted at the epsilon amino group of lysine as confirmed by NMR analysis, was extracted three times with chloroform. The solution was dried. After concentration, the solution was added drop by drop to diethyl ether to form a precipitate. The precipitate was collected and then crystallized from absolute ethanol. The percentage of modified amino groups was 53%, calculated by colorimetric analysis.

Step 2. Preparation of mPEG-Disubstituted Lysine. The mPEG-monosubstituted lysine product from step 1 above is soluble in organic solvents and so modification of the second lysine amino moiety can be achieved by reaction in dry methylene chloride. Activated mPEG, mPEG-p-nitrophenylcarbonate, is soluble and stable in organic solvents and can be used to modify the second lysine amino moiety.

Triethylamine ("TEA") was added to 4.5 grams of mPEG-monosubstituted lysine, which is about 0.86 millimoles. The mixture of TEA and mPEG-monosubstituted lysine was dissolved in 10 milliliters of anhydrous methylene chloride to reach a pH of 8.0. Four and nine tenths grams of mPEG-p-nitrophenycarbonate of molecular weight 5,000, which is 1.056 millimoles, was added over 3 hours to the solution. If it is desirable to make an mPEG disubstituted compound having mPEG arms of different lengths, then a different molecular weight mPEG could have been used. The pH was maintained at 8.0 with TEA. The reaction mixture was refluxed for 72 hours, brought to room temperature, concentrated, precipitated with diethyl ether and then crystallized in a minimum amount of hot ethanol. The excess of activated mPEG, mPEG-p-nitrophenycarbonate, was deactivated by hydrolysis in an alkaline aqueous medium by stirring overnight at room temperature. The solution was cooled to 0° C. and brought to a pH of about 3 with 2N HCl.

p-Nitrophenol was removed by extraction with diethyl ether. Monomethyl-poly(ethylene glycol)-disubstituted lysine and remaining traces of mPEG were extracted from the mixture three times with chloroform, dried, concentrated, precipitated with diethyl ether and crystallized from ethanol. No unreacted lysine amino groups remained in the polymer mixture as assessed by colorimetric analysis.

Purification of mPEG-disubstituted lysine and removal of mPEG were accomplished by gel filtration chromatography using a Bio Gel P100 (Bio-Rad) column. The column measured 5 centimeters by 50 centimeters. The eluent was water. Fractions of 10 milliliters were collected. Up to 200 milligrams of material could be purified for each run. The fractions corresponding to mPEG-disubstituted lysine were revealed by iodine reaction. These fractions were pooled, concentrated, and then dissolved in ethanol and concentrated. The mPEG-disubstituted lysine product was dissolved in methylene chloride, precipitated with diethyl ether, and crystallized from ethanol.

The mPEG-disubstituted lysine was also separated from unmodified mPEG—OH and purified by an alternative method. Ion exchange chromatography was performed on a QAE Sephadex A50 column (Pharmacia) that measured 5 centimeters by 80 centimeters. An 8.3 mM borate buffer of pH 8.9 was used. This alternative procedure permitted fractionation of a greater amount of material per run than the other method above described (up to four grams for each run).

For both methods of purification, purified mPEG-disubstituted lysine of molecular weight 10,000, titrated with NaOH, showed that 100% of the carboxyl groups were free carboxyl groups. These results indicate that the reaction was complete and the product pure.

The purified mPEG-disubstituted lysine was also characterized by $^1$H-NMR on a 200 MHz Bruker instrument in dimethyl sulfoxide, d6, at a 5% weight to volume concentration. The data confirmed the expected molecular weight of 10,000 for the polymer. The chemical shifts and assignments of the protons in the mPEG-disubstituted lysine are as follows: 1.2–1.4 ppm (multiplet, 6H, methylenes 3,4,5 of lysine); 1.6 ppm (multiplet, 2H, methylene 6 of lysine); 3.14 ppm (s, 3H, terminal mPEG methoxy); 3.49 ppm (s, mPEG backbone methylene); 4.05 ppm (t, 2H, —CH$_2$, —OCO—); 7.18 ppm (t, 1H, —NH— lysine); and 7.49 ppm (d,1 H, —NH— lysine).

The above signals are consistent with the reported structure since two different carbamate NH protons are present. The first carbamate NH proton (at 7.18 ppm) shows a triplet for coupling with the adjacent methylene group. The second carbamate NH proton (at 7.49 ppm) shows a doublet because of coupling with the α-CH of lysine. The intensity of these signals relative to the mPEG methylene peak is consistent with the 1:1 ratio between the two amide groups and the expected molecular weight of 10,000 for the polymer.

The two step procedure described above allows polymers of different types and different lengths to be linked with a single reactive site between them. The polymer can be designed to provide a polymer cloud of custom shape for a particular application.

The commercially available activated mPEG, mPEG-p-nitrophenylcarbonate, is available from Shearwater Polymers, Inc. in Huntsville, Ala. This compound was prepared by the following procedure, which can be represented structurally as follows:

mPEG$_a$—OH +

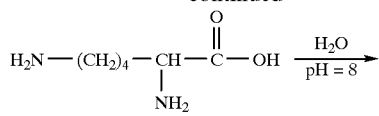

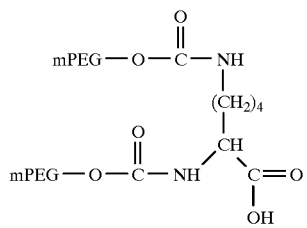

Five grams of mPEG—OH of molecular weight 5,000, or 1 millimole, were dissolved in 120 milliliters of toluene and dried azeotropically for 3 hours. The solution was cooled to room temperature and concentrated under vacuum. Reactants added to the concentrated solution under stirring at 0° C. were 20 milliliters of anhydrous methylene chloride and 0.4 g of p-nitrophenylchloroformate, which is 2 millimoles. The pH of the reaction mixture was maintained at 8 by adding 0.28 milliliters of triethylamine ("TEA"), which is 2 millimoles. The reaction mixture was allowed to stand overnight at room temperature. Thereafter, the reaction mixture was concentrated under vacuum to about 10 milliliters, filtered, and dropped into 100 milliliters of stirred diethyl ether. A precipitate was collected from the diethyl ether by filtration and crystallized twice from ethyl acetate. Activation of mPEG was determined to be 98%. Activation was calculated spectrophotometrically on the basis of the absorption at 400 nm in alkaline media after 15 minutes of released 4-nitrophenol (ε of p-nitrophenol at 400 nm equals 17,000).

B. One Step Procedure

In the one step procedure, mPEG disubstituted lysine is prepared from lysine and an activated mPEG in a single step as represented structurally below:

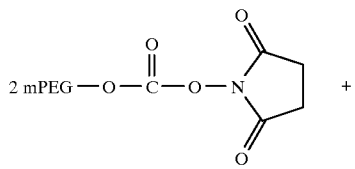

-continued

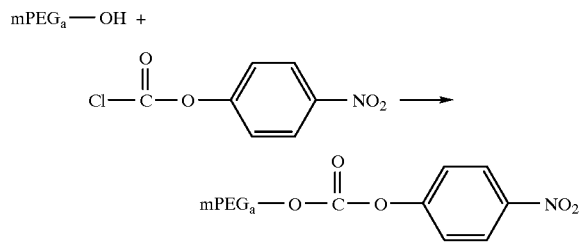

Except for molecular weight attributable to a longer PEG backbone in the activated mPEG used in the steps below, the mPEG disubstituted lysine of the one step procedure does not differ structurally from the mPEG disubstituted lysine of the two step procedure. It should be recognized that the identical compound, having the same molecular weight, can be prepared by either method.

Preparation of mPEG disubstituted lysine by the one step procedure proceeded as follows: Succinimidylcarbonate mPEG of molecular weight about 20,000 was added in an amount of 10.8 grams, which is $5.4 \times 10^{-4}$ moles, to 40 milliliters of lysine HCl solution. The lysine HCL solution was in a borate buffer of pH 8.0. The concentration was 0.826 milligrams succinimidylcarbonate mPEG per milliliter of lysine HCL solution, which is $1.76 \times 10^{-4}$ moles. Twenty milliliters of the same buffer was added. The solution pH was maintained at 8.0 with aqueous NaOH solution for the following 8 hours. The reaction mixture was stirred at room temperature for 24 hours.

Thereafter, the solution was diluted with 300 milliliters of deionized water. The pH of the solution was adjusted to 3.0 by the addition of oxalic acid. The solution was then extracted three times with dichloromethane. The combined dichloromethane extracts were dried with anhydrous sodium sulphate and filtered. The filtrate was concentrated to about 30 milliliters. The product, an impure mPEG disubstituted lysine, was precipitated with about 200 milliliters of cold ethyl ether. The yield was 90%.

Nine grams of the above impure mPEG-disubstituted lysine reaction product was dissolved in 4 liters of distilled water and then loaded onto a column of DEAE Sepharose FF, which is 500 milliliters of gel equilibrated with 1500 milliliters of boric acid in a 0.5% sodium hydroxide buffer at a pH of 7.0. The loaded system was then washed with water. Impurities of succinimidylcarbonate mPEG and mPEG-monosubstituted lysine, both of molecular weight about 20,000, were washed off the column. However, the desired mPEG disubstituted lysine of molecular weight 20,000 was eluted with 10 mM NaCl. The pH of the eluate was adjusted to 3.0 with oxalic acid and then mPEG disubstituted lysine was extracted with dichloromethane, dried with sodium sulphate, concentrated, and precipitated with ethyl ether. Five and one tenth grams of purified mPEG disubstituted lysine were obtained. The molecular weight was determined to be 38,000 by gel filtration chromatography and 36,700 by potentiometric titration.

The one step procedure is simple in application and is useful for producing high molecular weight dimers that have polymers of the same type and length linked with a single reactive site between them.

Additional steps are represented below for preparing succinimidylcarbonate mPEG for disubstitution of lysine.

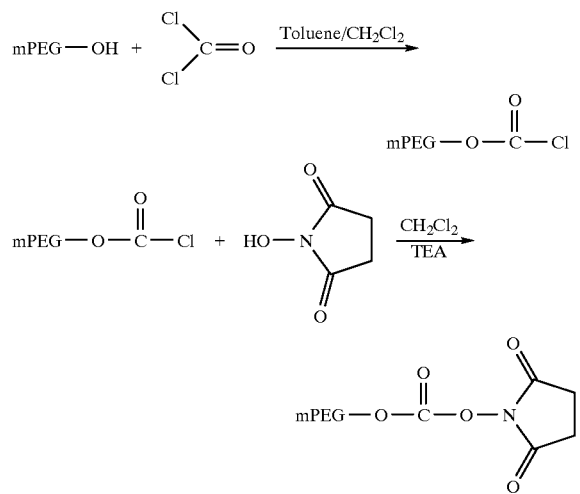

Succinimidylcarbonate mPEG was prepared by dissolving 30 grams of mPEG—OH of molecular weight 20,000, which is about 1.5 millimoles, in 120 milliliters of toluene. The solution was dried azeotropically for 3 hours. The dried solution was cooled to room temperature. Added to the cooled and dried solution were 20 milliliters of anhydrous dichloromethane and 2.33 milliliters of a 20% solution of phosgene in toluene. The solution was stirred continuously for a minimum of 16 hours under a hood due to the highly toxic fumes.

After distillation of excess phosgene and solvent, the remaining syrup, which contained mPEG chlorocarbonate, was dissolved in 100 milliliters of anhydrous dichloromethane, as represented above. To this solution was added 3 millimoles of triethylamine and 3 millimoles of N-hydroxysuccinimide. The reaction mixture remained standing at room temperature for 24 hours. Thereafter, the solution was filtered through a silica gel bed of pore size 60 Angstroms that had been wetted with dichloromethane. The filtrate was concentrated to 70 milliliters. Succinimidylcarbonate mPEG of molecular weight about 20,000 was precipitated in ethyl ether and dried in vacuum for a minimum of 8 hours. The yield was 90w. Succinimidylcarbonate-mPEG is available commercially from Shearwater Polymers in Huntsville, Ala.

The mPEG disubstituted lysine of the invention can be represented structurally more generally as $poly_a$—P—CR(—Q—$poly_b$)—Z or:

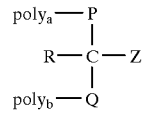

For the mPEG disubstituted lysines described above, —P—CR(—Q—)—Z is the reaction product of a precursor linker moiety having two reactive amino groups and active monofunctional precursors of $poly_a$ and $poly_b$ that have been joined to the linker moiety at the reactive amino sites. Linker fragments Q and P contain carbamate linkages formed by joining the amino containing portions of the lysine molecule with the functional group with which the mPEG was substituted. The linker fragments are selected from —O—C(O)NH(CH$_2$)$_4$— and —O—C(O)NH— and are different in the exemplified polymer derivative. However, it should be recognized that P and Q could both be —O—C(O)NH(CH$_2$)$_4$— or —O—C(O)NH— or some other linkage fragment, as discussed below. The moiety represented by R is hydrogen, H. The moiety represented by Z is the carboxyl group, —COOH. The moieties P, R, Q, and Z are all joined to a central carbon atom.

The nonpeptidic polymer arms, $poly_a$ and $poly_b$, are mPEG moieties $mPEG_a$ and $mPEG_b$, respectively, and are the same on each of the linker fragments Q and P for the examples above. The mPEG moieties have a structure represented as CH$_3$O—(CH$_2$CH$_2$O)$_n$CH$_2$CH$_2$—. For the mPEG disubstituted lysine made by the one step method, n is about 454 to provide a molecular weight for each mPEG moiety of 20,000 and a dimer molecular weight of 40,000. For the mPEG disubstituted lysine made by the two step method, n is about 114 to provide a molecular weight for each mPEG moiety of 5,000 and a dimer molecular weight of 10,000.

Lysine disubstituted with mPEG and having as dimer molecular weights of 10,000 and 40,000 and procedures for preparation of mPEG-disubstituted lysine have been shown. However, it should be recognized that mPEG disubstituted lysine and other multi-armed compounds of the invention can be made in a variety of molecular weights, including ultra high molecular weights. High molecular weight monofunctional PEGs are otherwise difficult to obtain.

Polymerization of ethylene oxide to yield mPEGs usually produces molecular weights of up to about 20,000 to 25,000 g/mol. Accordingly, two-armed mPEG disubstituted lysines of molecular weight of about 40,000 to 50,000 can be made according to the invention. Higher molecular weight lysine disubstituted PEGs can be made if the chain length of the linear mPEGs is increased, up to about 100,000. Higher molecular weights can also be obtained by adding additional monofunctional nonpeptidic polymer arms to additional reactive sites on a linker moiety, within practical limits of steric hindrance. However, no unreacted active sites on the linker should remain that could interfere with the mono-functionality of the multi-armed derivative. Lower molecular weight disubstituted mPEGs can also be made, if desired, down to a molecular weight of about 100 to 200.

It should be recognized that a wide variety of linker fragments P and Q are available, although not necessarily with equivalent results, depending on the precursor linker moiety and the functional moiety with which the activated mPEG or other nonpeptidic monofunctional polymer is substituted and from which the linker fragments result. Typically, the linker fragments will contain the reaction products of portions of linker moieties that have reactive amino and/or thiol moieties and suitably activated nonpeptidic, monofunctional, water soluble polymers.

For example, a wide variety of activated mPEGs are available that form a wide variety of hydrolytically stable linkages with reactive amino moieties. Linkages can be selected from the group consisting of amide, amine, ether, carbamate, which are also called urethane linkages, urea, thiourea, thiocarbamate, thiocarbonate, thioether, thioester, dithiocarbonate linkages, and others. However, hydrolytically weak ester linkages and potentially toxic aromatic moieties are to be avoided.

Hydrolytic stability of the linkages means that the linkages between the polymer arms and the linker moiety are stable in water and that the linkages do not react with water at useful pHs for an extended period of time of at least several days, and potentially indefinitely. Most proteins could be expected to lose their activity at a caustic pH of 11 or higher, so the derivatives should be stable at a pH of less than about 11.

Examples of the above linkages and their formation from activated mPEG and lysine are represented structurally below.

a) Formation of Amide Linkage i) 2 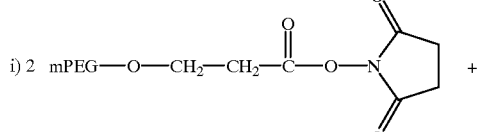 +

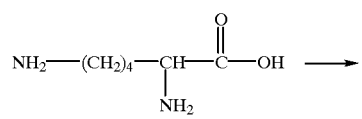 →

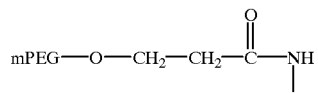

ii) 2 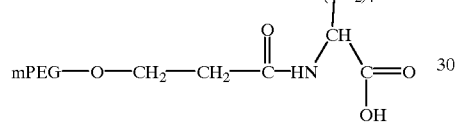 +

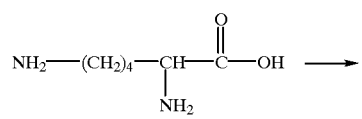 →

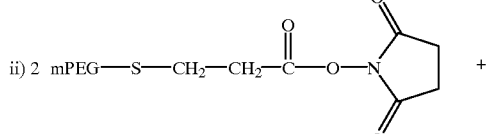

iii) 2 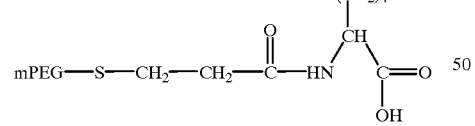 +

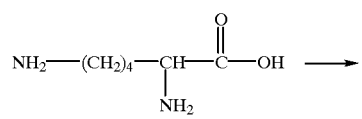 → iv) 2 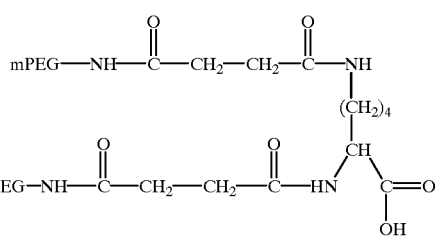 +

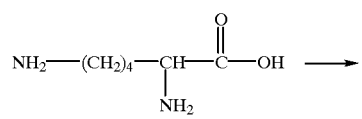 →

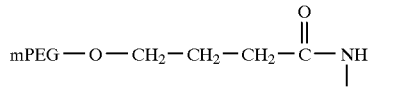

b) Formation of Carbamate Linkage

2 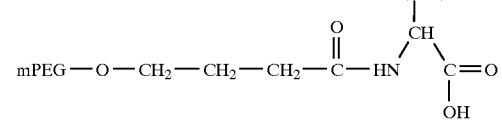 +

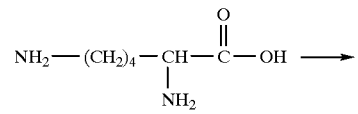 →

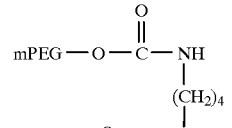

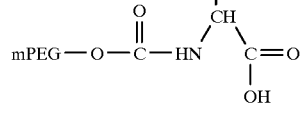

c) Formation of Urea Linkage

2 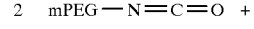 +

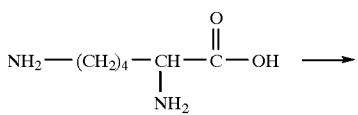 →

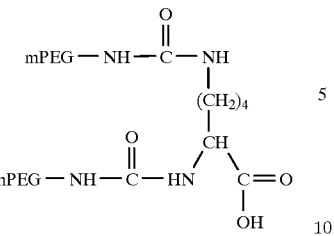

d) Formation of Thiourea Linkage

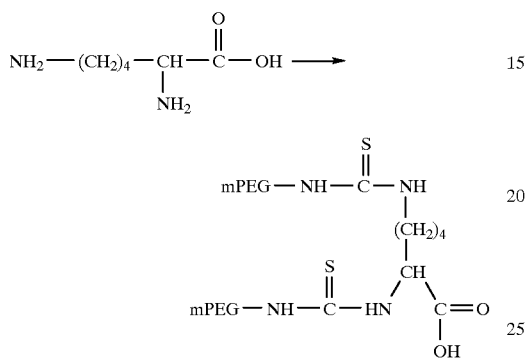

e) Formation of Amine Linkage

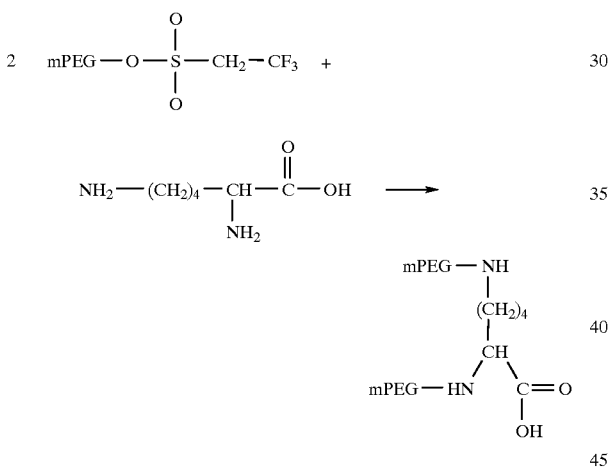

One or both of the reactive amino moieties, —NH₂, of lysine or another linker moiety can be replaced with thiol moieties, —SH. Where the linker moiety has a reactive thiol moiety instead of an amino moiety, then the linkages can be selected from the group consisting of thioester, thiocarbonate, thiocarbamate, dithiocarbamate, thioether linkages, and others. The above linkages and their formation from activated mPEG and lysine in which both amino moieties have been replaced with thiol moieties are represented structurally below.

a) Formation of Thioester Linkage

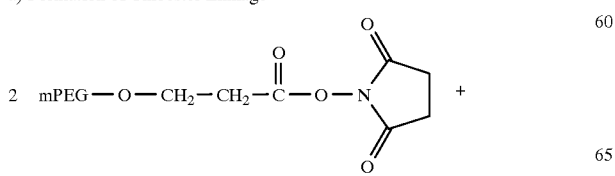

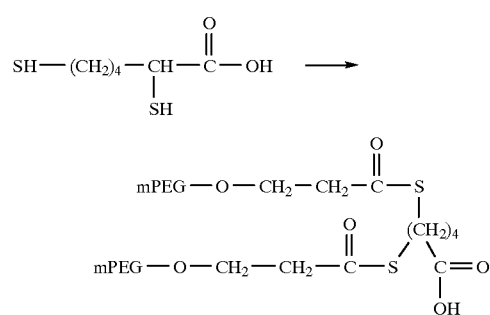

b) Formation of Thiocarbonate Linkage

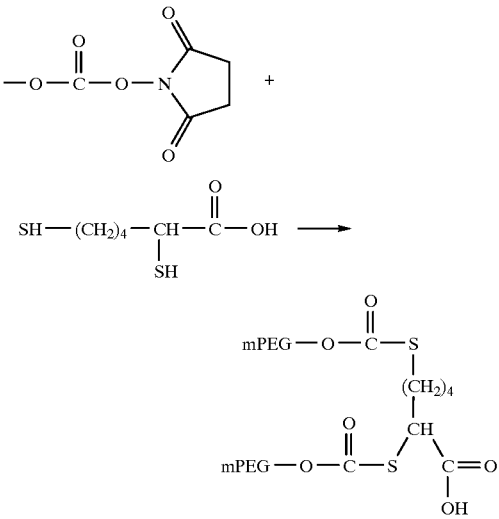

c) Formation of Thiocarbonate Linkage

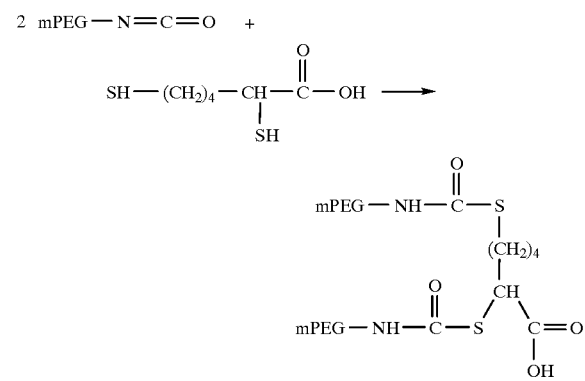

d) Formation of Dithiocarbamate Linkage

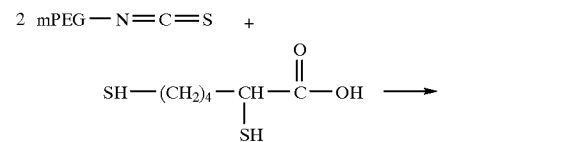

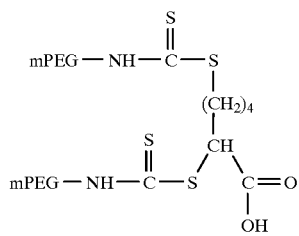

e) Formation of Thioether Linkage

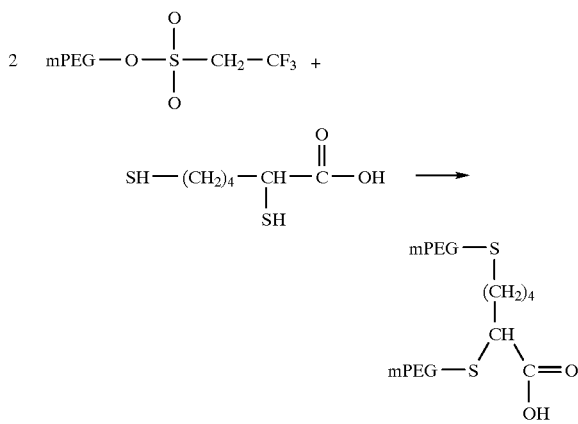

It should be apparent that the mPEG or other monofunctional polymer reactants can be prepared with a reactive amino moiety and then linked to a suitable linker moiety having reactive groups such as those shown above on the mPEG molecule to form hydrolytically stable linkages as discussed above. For example, the amine linkage could be formed as follows:

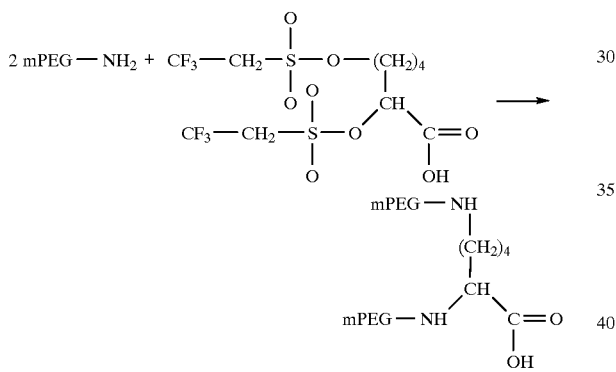

Examples of various active electrophilic moieties useful for activating polymers or linking moieties for biological and biotechnical applications in which the active moiety is reacted to form hydrolytically stable linkages in the absence of aromatic moieties include trifluoroethylsulfonate, isocyanate, isosthiocyanate, active esters, active carbonates, various aldehydes, various sulfones, including chloroethylsulfone and vinylsulfone, maleimide, iodoacetamide, and iminoesters. Active esters include N-hydroxylsuccinimidyl ester. Active carbonates include N-hydroxylsuccinimidyl carbonate, p-nitrophenylcarbonate, and trichlorophenylcarbonate. These electrophilic moieties are examples of those that are suitable as Ws in the structure poly-W and as Xs and Ys in the linker structure X—CR(—Y)—Z.

Nucleophilic moieties for forming the linkages can be amino, thiol, and hydroxyl. Hydroxyl moieties form hydrolytically stable linkages with isocyanate electrophilic moieties. Also, it should be recognized that the linker can be substituted with different nucleophilic or electrophilic moieties or both electrophilic and nucleophilic moieties depending on the active moieties on the monofunctional polymers with which the linker moiety is to be substituted.

Linker moieties other than lysine are available for activation and for disubstitution or multisubstitution with mPEG and related polymers for creating multi-armed structures in the absence of aromatic moieties in the structure and that are hydrolytically stable. Examples of such linker moieties include those having more than one reactive site for attachment of various monofunctional polymers.

Linker moieties can be synthesized to include multiple reactive sites such as amino, thiol, or hydroxyl groups for joining multiple suitably activated mPEGs or other nonpeptidic polymers to the molecule by hydrolytically stable linkages, if it is desired to design a molecule having multiple nonpeptidic polymer branches extending from one or more of the linker arm fragments. The linker moieties should also include a reactive site, such as a carboxyl or alcohol moiety, represented as —Z in the general structure above, for which the activated polymers are not selective and that can be subsequently activated for selective reactions for joining to enzymes, other proteins, surfaces, and the like.

For example, one suitable linker moiety is a diamino alcohol having the structure

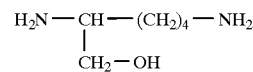

The diamino alcohol can be disubstituted with activated mPEG or other suitable activated polymers similar to disubstitution of lysine and then the hydroxyl moiety can be activated as follows:

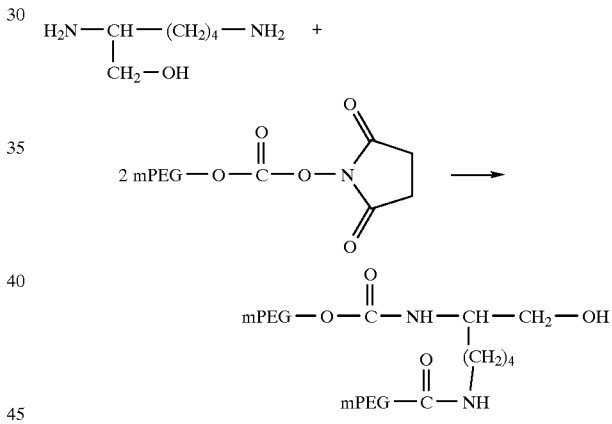

Other diamino alcohols and alcohols having more than two amino or other reactive groups for polymer attachment are useful. A suitably activated mPEG or other monofunctional, nonpeptidic, water soluble polymer can be attached to the amino groups on such a diamino alcohol similar to the method by which the same polymers are attached to lysine as shown above. Similarly, the amino groups can be replaced with thiol or other active groups as discussed above. However, only one hydroxyl group, which is relatively nonreactive, should be present in the —Z moiety, and can be activated subsequent to polymer substitution.

The moiety —Z can include a reactive moiety or functional group, which normally is a carboxyl moiety, hydroxyl moiety, or activated carboxyl or hydroxyl moiety. The carboxyl and hydroxyl moieties are somewhat nonreactive as compared to the thiol, amino, and other moieties discussed above. The carboxyl and hydroxyl moieties typically remain intact when the polymer arms are attached to the linker moiety and can be subsequently activated. The carboxyl and hydroxyl moieties also provide a mechanism for purification of the multisubstituted linker moiety. The carboxyl and hydroxyl moieties provide a site for interacting with ion exchange chromatography media.

The moiety —Z may also include a linkage fragment, represented as $R_Z$ in the moiety, which can be substituted or unsubstituted, branched or linear, and joins the reactive moiety to the central carbon. Where a reactive group of the —Z moiety is carboxyl, for activation after substitution with nonpeptidic polymers, then the —Z moiety has the structure —$R_Z$—COOH if the Rz fragment is present. For hydroxyl, the structure is —$R_Z$—OH. For example, in the diamino alcohol structure discussed above, $R_Z$ is $CH_2$. It should be understood that the carboxyl and hydroxyl moieties normally will extend from the $R_Z$ terminus, but need not necessarily do so.

$R_Z$ can also include the reaction product of one or more reactive moieties including reactive amino, thiol, or other moieties, and a suitably activated mPEG arm or related nonpeptidic polymer arm. In the latter event, $R_Z$ can have the structure (—L—$poly_c$)—COOH or (—L—$poly_c$)—OH in which —L— is the reaction product of a portion of the linker moiety and a suitably activated nonpeptidic polymer, $poly_c$—W, which is selected from the same group as $poly_a$—W and $poly_b$—W but can be the same or different from $poly_a$—W and $poly_b$—W.

It is intended that —Z have a broad definition. The moiety —Z is intended to represent not only the reactive site of the multisubstituted polymeric derivative that subsequently can be converted to an active form and its attachment to the central carbon, but the activated reactive site and also the conjugation of the precursor activated site with another molecule, whether that molecule be an enzyme, other protein or polypeptide, a phospholipid, a preformed liposome, or on a surface to which the polymer derivative is attached.

The skilled artisan should recognize that Z encompasses the currently known activating moieties in PEG chemistry and their conjugates. It should also be recognized that, although the linker fragments represented by Q and P and $R_Z$ should not contain aromatic rings or hydrolytically weak linkages such as ester linkages, such rings and such hydrolytically weak linkages may be present in the active site moiety of —Z or in a molecule joined to such active site. It may be desirable in some instances to provide a linkage between, for example, a protein or enzyme and a multisubstituted polymer derivative that has limited stability in water. Some amino acids contain aromatic moieties, and it is intended that the structure Z include conjugates of multisubstituted monofunctional polymer derivatives with such molecules or portions of molecules. Activated Zs and Zs including attached proteins and other moieties are discussed below.

When lysine, the diamino alcohol shown above, or many other compounds are linkers, then the central carbon has a nonreactive hydrogen, H, attached thereto. In the general structure $poly_a$—P—CR(—Q—$poly_b$)—Z, R is H. It should be recognized that the moiety R can be designed to have another substantially nonreactive moiety, such as a nonreactive methyl or other alkyl group, or can be the reaction product of one or more reactive moieties including reactive amino, thiol, or other moieties, and a suitably activated mPEG arm or related nonpeptidic polymer arm. In the latter event, R can have the structure —M—$poly_d$, in which —M— is the reaction product of a portion of the linker moiety and a suitably activated nonpeptidic polymer, $poly_a$—W, which is selected from the same group as $poly_a$—W and $poly_b$—W but can be the same or different from $poly_a$—W and $poly_b$—W.

For example, multi-armed structures can be made having one or more mPEGs or other nonpeptidic polymer arms extending from each portion P, Q, R, and $R_Z$, all of which portions extend from a central carbon atom, C, which multi-armed structures have a single reactive site for subsequent activation included in the structure represented by Z. Upon at least the linker fragments P and Q are located at least one active site for which the monofunctional, nonpeptidic polymers are selective. These active sites include amino moieties, thiol moieties, and other moieties as described above.

The nonpeptidic polymer arms tend to mask antigenic properties of the linker fragment, if any. A linker fragment length of from 1 to 10 carbon atoms or the equivalent has been determined to be useful to avoid a length that could provide an antigenic site. Also, for all the linker fragments P, Q, R, and $R_Z$, there should be an absence of aromatic moieties in the structure and the linkages should be hydrolytically stable.

Poly(ethylene glycol) is useful in the practice of the invention for the nonpeptidic polymer arms attached to the linker fragments. PEG is used in biological applications because it has properties that are highly desirable and is generally approved for biological or biotechnical applications. PEG typically is clear, colorless, odorless, soluble in water, stable to heat, inert to many chemical agents, does not hydrolyze or deteriorate, and is nontoxic. Poly(ethylene glycol) is considered to be biocompatible, which is to say that PEG is capable of coexistence with living tissues or organisms without causing harm. More specifically, PEG is not immunogenic, which is to say that PEG does not tend to produce an immune response in the body. When attached to a moiety having some desirable function in the body, the PEG tends to mask the moiety and can reduce or eliminate any immune response so that an organism can tolerate the presence of the moiety. Accordingly, the activated PEGs of the invention should be substantially non-toxic and should not tend substantially to produce an immune response or cause clotting or other undesirable effects.

The term "PEG" is used in the art and herein to describe any of several condensation polymers of ethylene glycol having the general formula represented by the structure $$HO-(CH_2CH_2O)_nCH_2CH_2-OH$$

or, more simply, as HO—PEG—OH. PEG is also known as polyoxyethylene, polyethylene oxide, polyglycol, and polyether glycol. PEG can be prepared as copolymers of ethylene oxide and many other monomers.

Other water soluble polymers than PEG are suitable for similar modification to create multi-armed structures that can be activated for selective reactions. These other polymers include poly(vinyl alcohol) ("PVA"); other poly (alkylene oxides) such as poly(propylene glycol) ("PPG") and the like; and poly(oxyethylated polyols) such as poly (oxyethylated glycerol), poly(oxyethylated sorbitol), and poly(oxyethylated glucose), and the like. The polymers can be homopolymers or random or block copolymers and terpolymers based on the monomers of the above polymers, straight chain or branched, or substituted or unsubstituted similar to mPEG and other capped, monofunctional PEGs having a single active site available for attachment to a linker.

Specific examples of suitable additional polymers include poly(oxazoline), poly(acryloylmorpholine) ("PAcM"), and poly(vinylpyrrolidone)("PVP"). PVP and poly(oxazoline) are well known polymers in the art and their preparation and use in the syntheses described above for mPEG should be readily apparent to the skilled artisan.

An example of the synthesis of a PVP disubstituted lysine having a single carboxyl moiety available for activation is shown below. The disubstituted compound can be purified, activated, and used in various reactions for modification of molecules and surfaces similarly to the mPEG-disubstituted lysine described above.

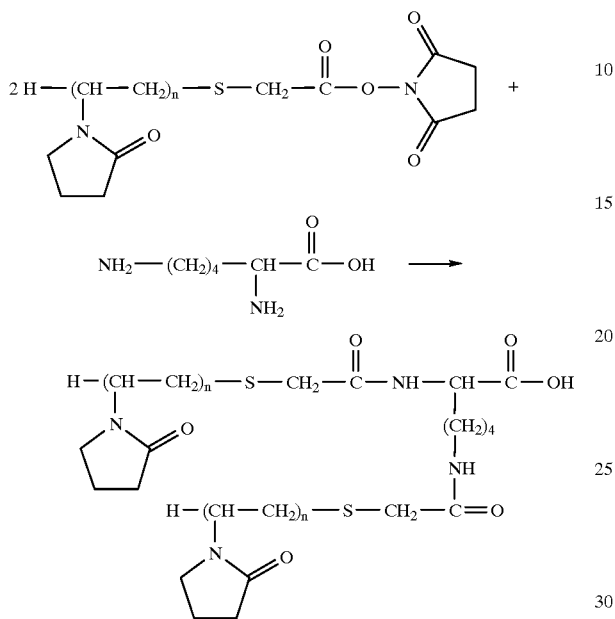

Poly(acryloylmorpholine) "(PAcM)" functionalized at one end is a new polymer, the structure, preparation, and characteristics of which are described in Italian Patent Application No. MI 92 A 0002616, which was published May 17, 1994 and is entitled, in English, "*Polymers Of N-Acryloylmorpholine Functionalized At One End And Conjugates With Bioactive Materials And Surfaces.*" Dimer polymers of molecular weight up to at least about 80,000 can be prepared using this polymer. The contents of the Italian patent application are incorporated herein by reference.

PAcM can be used similarly to mPEG or PVP to create multi-armed structures and ultra-high molecular weight polymers. An example of a PAcM-disubstituted lysine having a single carboxyl moiety available for activation is shown below. The disubstituted compound can be purified, activated, and used in various reactions for modification of molecules and surfaces similarly to the mPEG- and PVP-disubstituted lysines described above.

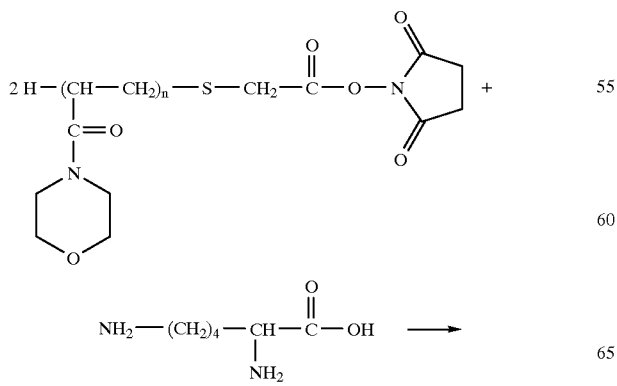

-continued

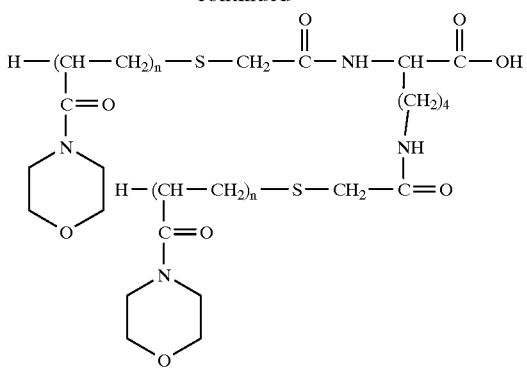

It should also be recognized that the multi-armed monofunctional polymers of the invention can be used for attachment to a linker moiety to create a highly branched monofunctional structure, within the practical limits of steric hindrance.

II. Activation of mPEG-Disubstituted Lysine and Modification of Protein Amino Groups.

Schemes are represented below for activating the mPEG-disubstituted lysine product made by either the one step or two step procedures and for linking the activated mPEG-disubstituted lysine through a stable carbamate linkage to protein amino groups to prepare polymer and protein conjugates. Various other multisubstituted polymer derivatives as discussed above can be activated similarly.

A. Activation of mPEG Disubstituted Lysine.

Purified mPEG-disubstituted lysine produced in accordance with the two step procedure discussed above was activated with N-hydroxysuccinimide to produce mPEG-disubstituted lysine activated as the succinimidyl ester. The reaction is represented structurally below:

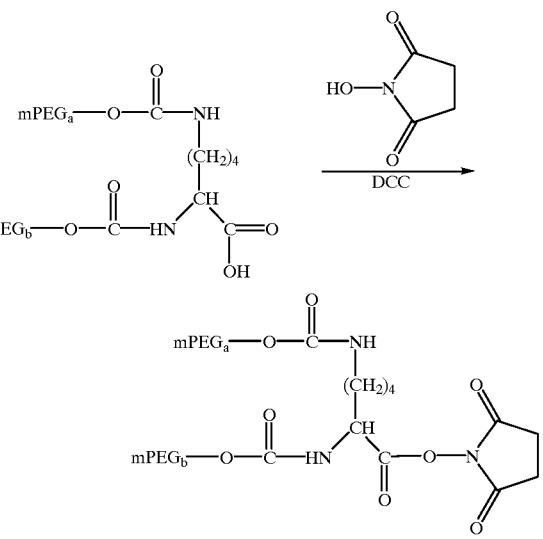

Six and two tenths grams of mPEG-disubstituted lysine of molecular weight 10,000, which is about 0.6 millimoles, was dissolved in 10 milliliters of anhydrous methylene chloride and cooled to 0° C. N-hydroxysuccinimide and N,N-dicyclohexylcarbodiimide ("DCC") were added under stirring in the amounts, respectively, of 0.138 milligrams, which is about 1.2 millimoles, and 0.48 milligrams, which is about 1.2 millimoles. The reaction mixture was stirred overnight at room temperature. Precipitated dicyclohexylurea was removed by filtration and the solution was concentrated and precipitated with diethyl ether. The product, mPEG disubstituted lysine activated as the succinimidyal ester, was crystallized from ethyl acetate. The yield of esterification, calculated on the basis of hydroxysuccinimide absorption at 260 nm (produced by hydrolysis), was over 97% ($\epsilon$ of hydroxysuccinimide at 260 nm=8,000 $m^{-1}cm^{-1}$) The NMR spectrum was identical to that of the unactivated carboxylic acid except for the new succinimide singlet at 2.80 ppm (2Hs)

The procedure previously described for the activation of the mPEG-disubstituted lysine of molecular weight 10,000 was also followed for the activation of the higher molecular weight polymer of molecular weight approximately 40,000 that was produced in accordance with the one step procedure discussed above. The yield was over 95%. of high molecular weight mPEG-disubstituted lysine activated as the succinimidyal ester.

It should be recognized that a number of activating groups can be used to activate the multisubstituted polymer derivatives for attachment to surfaces and molecules. Any of the activating groups of the known derivatives of PEG can be applied to the multisubstituted structure. For example, the mPEG-disubstituted lysine of the invention was functionalized by activation as the succinimidyl ester, which can be attached to protein amino groups. However, there are a wide variety of functional moieties available for activation of carboxilic acid polymer moieties for attachment to various surfaces and molecules. Examples of active moieties used for biological and biotechnical applications include trifluoroethylsulfonate, isocyanate, isosthiocyanate, active esters, active carbonates, various aldehydes, various sulfones, including chloroethylsulfone and vinylsulfone, maleimide, iodoacetamide, and iminoesters. Active esters include N-hydroxylsuccinimidyl ester. Active carbonates include N-hydroxylsuccinimidyl carbonate, p-nitrophenylcarbonate, and trichlorophenylcarbonate.

A highly useful, new activating group that can be used for highly selective coupling with thiol moieties instead of amino moieties on molecules and surfaces is the vinyl sulfone moiety described in U.S. Pat. No. 5,446,090, which issued Aug. 29, 1995, the contents of which are incorporated herein by reference. Various sulfone moieties can be used to activate a multi-armed structure in accordance with the invention for thiol selective coupling.

Various examples of activation of —Z reactive moieties to created —Z activated moieties are presented as follows:

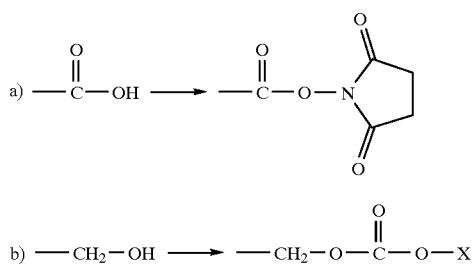

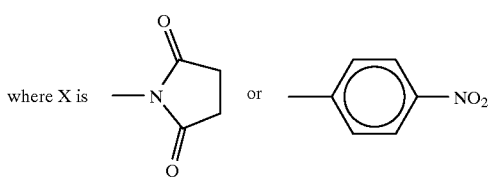

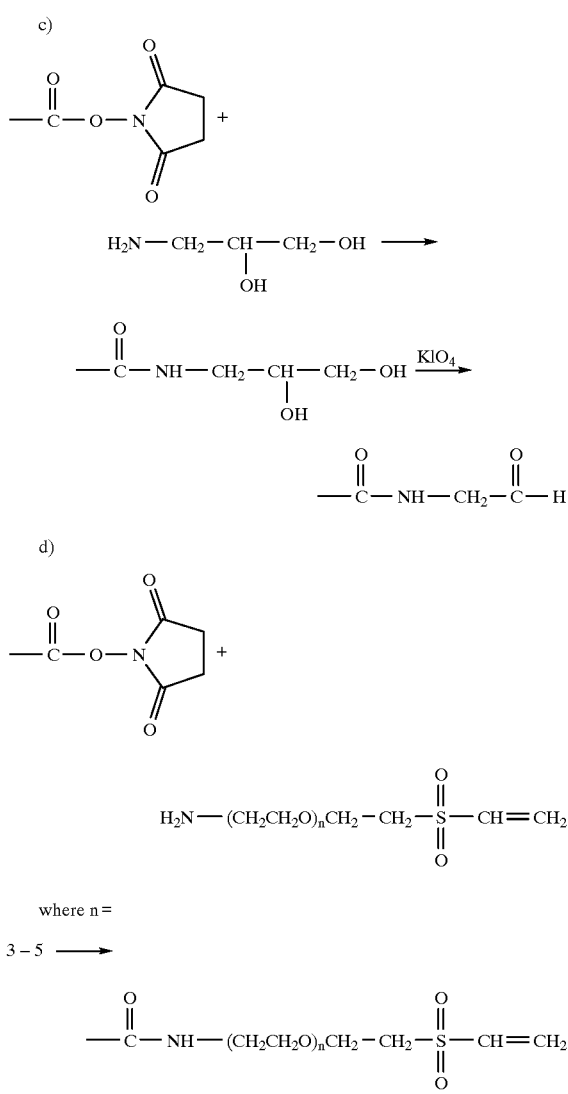

It should also be recognized that, although the linker fragments represented by Q and P should not contain aromatic rings or hydrolytically weak linkages such as ester linkages, such rings and such hydrolytically weak linkages may be present in the moiety represented by —Z. It may be desirable in some instances to provide a linkage between, for example, a protein or enzyme and a multisubstituted polymer derivative that has limited stability in water. Some amino acids contain aromatic moieties, and it is intended that the structure —Z include conjugates of multisubstituted monofunctional polymer derivatives with such molecules or portions of molecules.

B. Enzyme Modification

Enzymes were modified with activated, two-armed, mPEG-disubstituted lysine of the invention of molecular weight about 10,000 that had been prepared according to the two step procedure and activated as the succinimidyl ester as discussed above. The reaction is represented structurally below:

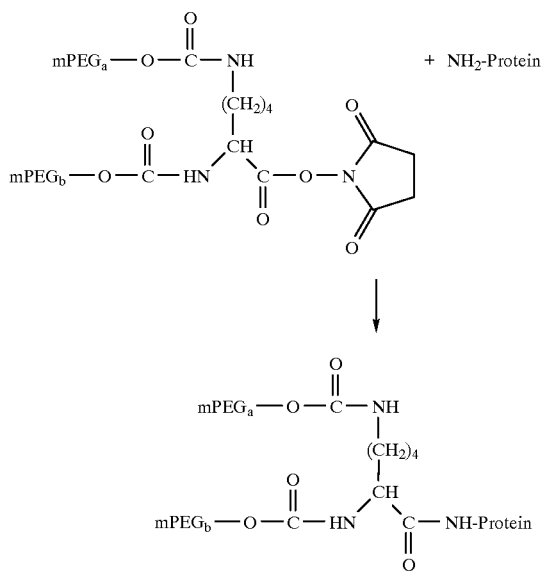

For comparison, enzymes were also modified with activated, conventional, linear mPEG of molecular weight 5,000, which was mPEG with a norleucine amino acid spacer arm activated as the succinimide. In the discussion of enzyme modification below, conventional, linear mPEG derivatives with which enzymes are modified are referred to as "linear mPEG." The activated, two-armed, mPEG-disubstituted lysine of the invention is referred to as "two-armed mPEG." Different procedures were used for enzyme modification depending upon the type of enzyme and the polymer used so that a similar extent of amino group modification or attachment for each enzyme could be obtained. Generally, higher molar ratios of the two-armed mPEG were used. However, in all examples the enzymes were dissolved in a 0.2M borate buffer of pH 8.5 to dissolve proteins. The polymers were added in small portions for about 10 minutes and stirred for over 1 hour. The amount of polymer used for modification was calculated on the basis of available amino groups in the enzyme.

Ribonuclease in a concentration of 1.5 milligrams per milliliter of buffer was modified at room temperature. Linear and two-armed mPEGs as described were added at a molar ratio of polymer to protein amino groups of 2.5:1 and 5:1, respectively. Ribonuclease has a molecular weight of 13,700 D and 11 available amino groups. Catalase has a molecular weight of 250,000 D with 112 available amino groups. Trypsin has a molecular weight of 23,000 D with 16 available amino groups. Erwinia Caratimora asparaginase has a molecular weight of 141,000 D and 92 free amino groups.

Catalase in a concentration of 2.5 milligrams per milliliter of buffer was modified at room temperature. Linear and two-armed mPEGs as described were added at a molar ratio of polymer to protein amino groups of 5:1 and 10:1, respectively.

Trypsin in a concentration of 4 milligrams per milliliter of buffer was modified at 0° C. Linear and two-armed mPEGs as described were added at a molar ratio of polymer to protein amino groups of 2.5:1.

Asparaginase in a concentration of 6 milligrams per milliliter of buffer was modified with linear mPEG at room temperature. Linear mPEG as described was added at a molar ratio of polymer to protein amino groups of 3:1. Asparaginase in a concentration of 6 milligrams per milliliter of buffer was modified with two-armed mPEG at 37° C. Two-armed mPEG of the invention as described was added at a molar ratio of polymer to protein amino groups of 3.3:1.

The polymer and enzyme conjugates were purified by ultrafiltration and concentrated in an Amicon system with a PM 10 membrane (cut off 10,000) to eliminate N-hydroxysuccinimide and reduce polymer concentration. The conjugates were further purified from the excess of unreacted polymer by gel filtration chromatography on a Pharmacia Superose 12 column, operated by an FPLC instrument, using 10 mM phosphate buffer of pH 7.2, 0.15M in NaCl, as eluent.

Protein concentration for the native forms of ribonuclease, catalase, and trypsin was evaluated spectrophotometrically using molar extinction coefficients of 945× $10^3 M^{-1}$ $cm^{-1}$, $1.67 \times 10^5 M^{-1}$ $cm^{-1}$ and $3.7 \times 10^4 M^{-1}$ $cm^{-1}$ at 280 nm, respectively. The concentration of native asparaginase was evaluated by biuret assay. Biuret assay was also used to evaluate concentrations of the protein modified forms.

The extent of protein modification was evaluated by one of three methods. The first is a calorimetric method described in Habeeb, A. F. S. A. (1966) Determination of free amino groups in protein by trinitrobenzensulphonic acid. *Anal. Biochem.* 14, 328–336. The second method is amino acid analysis after acid hydrolysis. This method was accomplished by two procedures: 1) the post-column procedure of Benson, J. V., Gordon, M. J., and Patterson, J. A. (1967) Accelerated chromatographic analysis of amino acid in physiological fluids containing vitamin and asparagine. *Anal. Biol. Chem.* 18, 288–333, and 2) pre-column derivatization by phenylisothiocyanate (PITC) according to Bidlingmeyer, B. A., Cohen, S. A., and Tarvin, T. L. (1984) Rapid analysis of amino acids using pre-column derivatization. *J. Chromatography* 336, 93–104.

The amount of bound linear mPEG was evaluated from norleucine content with respect to other protein amino acids. The amount of two-armed, mPEG-disubstituted lysine was determined from the increase in lysine content. One additional lysine is present in the hydrolysate for each bound polymer.

III. Analysis of Polymer and Enzyme Conjugates

Five different model enzymes, ribonuclease, catalase, asparaginase, trypsin and uricase, were modified with linear, conventional mPEG of molecular weight 5000 having a norleucine amino acid spacer arm activated as succinimidyl ester and with a two-armed, mPEG-disubstituted lysine of the invention prepared from the same linear, conventional mPEG as described above in connection with the two step procedure. The molecular weight of the two-armed mPEG disubstituted lysine of the invention was approximately 10,000.

A. Comparison of Enzyme Activity. The catalytic properties of the modified enzymes were determined and compared and the results are presented in Table 1 below. To facilitate comparison, each enzyme was modified with the two polymers to a similar extent by a careful choice of polymer to enzyme ratios and reaction temperature.

Ribonuclease with 50% and 55% of the amino groups modified with linear mPEG and two-armed mPEG, respectively, presented 86% and 94% residual activity with respect to the native enzyme. Catalase was modified with linear mPEG and with two-armed mPEG to obtain 43% and 38% modification of protein amino groups, respectively. Enzyme activity was not significantly changed after modification. Trypsin modification was at the level of 50% and 57% of amino groups with linear mPEG and with two-armed mPEG, respectively. Esterolytic activity for enzyme modified with linear mPEG and two-armed mPEG, assayed on the small substrate TAME, was increased by the modification to 120% and 125%, respectively. Asparaginase with 53% and 40% modified protein amino groups was obtained by coupling with linear mPEG and two-armed mPEG, respectively. Enzymatic activity was increased, relative to the free enzyme, to 110% for the linear mPEG conjugate and to 133% for the two-armed mPEG conjugate.

While not wishing to be bound by theory, it is possible that in the case of trypsin and asparaginase, that modification produces a more active form of the enzyme. The $K_m$ values of the modified and unmodified forms are similar.

For the enzyme uricase a particularly dramatic result was obtained. Modification of uricase with linear mPEG resulted in total loss of activity. While not wishing to be bound by theory, it is believed that the linear mPEG attached to an amino acid such as lysine that is critical for activity. In direct contrast, modification of 40% of the lysines of uricase with two-armed mPEG gave a conjugate retaining 70% activity.

It is apparent that modification of enzymes with two-armed mPEG gives conjugates of equal or greater activity than those produced by conventional linear mPEG modification with monosubstituted structures, despite the fact that two-armed mPEG modification attaches twice as much polymer to the enzyme.

Coupling two-armed mPEG to asparaginase with chlorotriazine activation as described in the background of the invention gave major loss of activity. Presumably the greater activity of enzymes modified with a two-armed mPEG of the invention results because the bulky two-armed mPEG structure is less likely than monosubstituted linear mPEG structures to penetrate into active sites of the proteins.

TABLE 1

Properties of enzymes modified by linear mPEG and two-armed mPEG.

| ENZYME[a] | $NH_2$:POLY-MER MOLAR RATIO | % MODIFICATION | % ACTIVITY | Km (M) | Kcas (min$^{-1}$) |
|---|---|---|---|---|---|
| Ribonuclease | | | | | |
| RN | 1:0 | 0 | 100 | | |
| RP1 | 1:2.5 | 50 | 86 | | |
| RP2 | 1:5 | 55 | 94 | | |
| Catalase | | | | | |
| CN | 1:0 | 0 | 100 | | |
| CP1 | 1:5 | 43 | 100 | | |
| CP2 | 1:10 | 38 | 90 | | |
| Trypsin[b] | | | | | |
| TN | 1:0 | 0 | 100 | $8.2 \times 10^{-5}$ | 830 |
| TP1 | 1:2.5 | 50 | 120 | $7.6 \times 10^{-5}$ | 1790 |
| TP2 | 1:2.5 | 57 | 125 | $8.0 \times 10^{-5}$ | 2310 |
| Asparaginase | | | | | |
| AN | 1:0 | 0 | 100 | $3.31 \times 10^{-6}$ | 523 |
| AP1 | 1:3 | 53 | 110 | $3.33 \times 10^{-6}$ | 710 |
| AP2 | 1:3.3 | 40 | 133 | $3.30 \times 10^{-6}$ | 780 |
| Uricase | | | | | |
| UP | 1:0 | 0 | 100 | | |
| UP1 | 1:5 | 45 | 0 | | |
| UP2 | 1:10 | 40 | 70 | | |

[a]N = native enzyme, P1 = enzyme modified with linear mPEG, P2 = enzyme modified with two-armed mPEG.
[b]For trypsin only the esterolytic activity is reported.

Enzymatic activity of native and modified enzyme was evaluated by the following methods. For ribonuclease, the method was used of Crook, E. M., Mathias, A. P., and Rabin, B. R. (1960) Spectrophotometric assay of bovine pancreatic ribonuclease by the use of cytidine 2':3' phosphate. *Biochem. J.* 74, 234–238. Catalase activity was determined by the method of Beers, R. F. and Sizer, I. W. (1952) A spectrophotometric method for measuring the breakdown of hydrogen peroxide by catalase. *J. Biol. Chem.* 195,133–140. The esterolytic activity of trypsin and its derivatives was determined by the method of Laskowski, M. (1955) Tryosinogen and tryosin. *Methods Enzyymol.* 2, 26–36. Native and modified asparaginase were assayed according to a method reported by Cooney, D. A., Capizzi, R. L. and Handschumacher, R. E. (1970) Evaluation of L-asparagine metabolism in animals and man. *Cancer Res.* 30, 929–935. In this method, 1.1 ml containing 120 μg of α-ketoglutaric acid, 20 Ul of glutamic-oxalacetic transaminase, 30 Ul of malate dehydrogenase, 100 μg of NADH, 0.5 μg of asparaginase and 10 μmoles of asparagine were incubated in 0.122M Tris buffer, pH 8.35, while the NADH absorbance decrease at 340 nm was followed.

B. Proteolytic Digestion of Free Enzyme and Conjugates.
The rates at which proteolytic enzymes digest and destroy proteins was determined and compared for free enzyme, enzyme modified by attachment of linear activated mPEG, and enzyme modified by attachment of an activated two-armed mPEG of the invention. The proteolytic activities of the conjugates were assayed according to the method of Zwilling, R., and Neurath, H. (1981) Invertrebate protease. *Methods Enzymol.* 80, 633–664. Four enzymes were used: ribonuclease, catalase, trypsin, and asparaginase. From each enzyme solution, aliquots were taken at various time intervals and enzyme activity was assayed spectrophotometrically.

Proteolytic digestion was performed in 0.05M phosphate buffer of pH 7.0. The free enzyme, linear mPEG and protein conjugate, and two-armed mPEG-protein conjugates were exposed to the known proteolytic enzymes trypsin, pronase, elastase or subtilisin under conditions as follows.

Figure 1B:
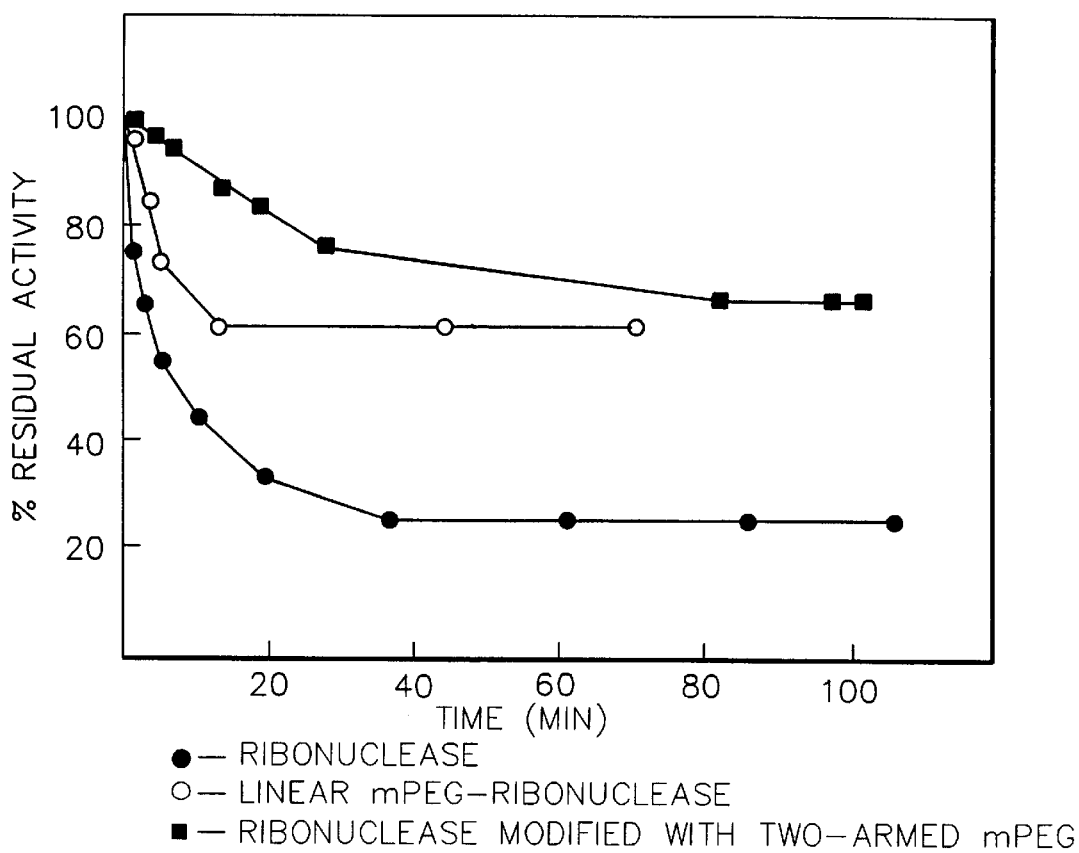
Figure 1C:
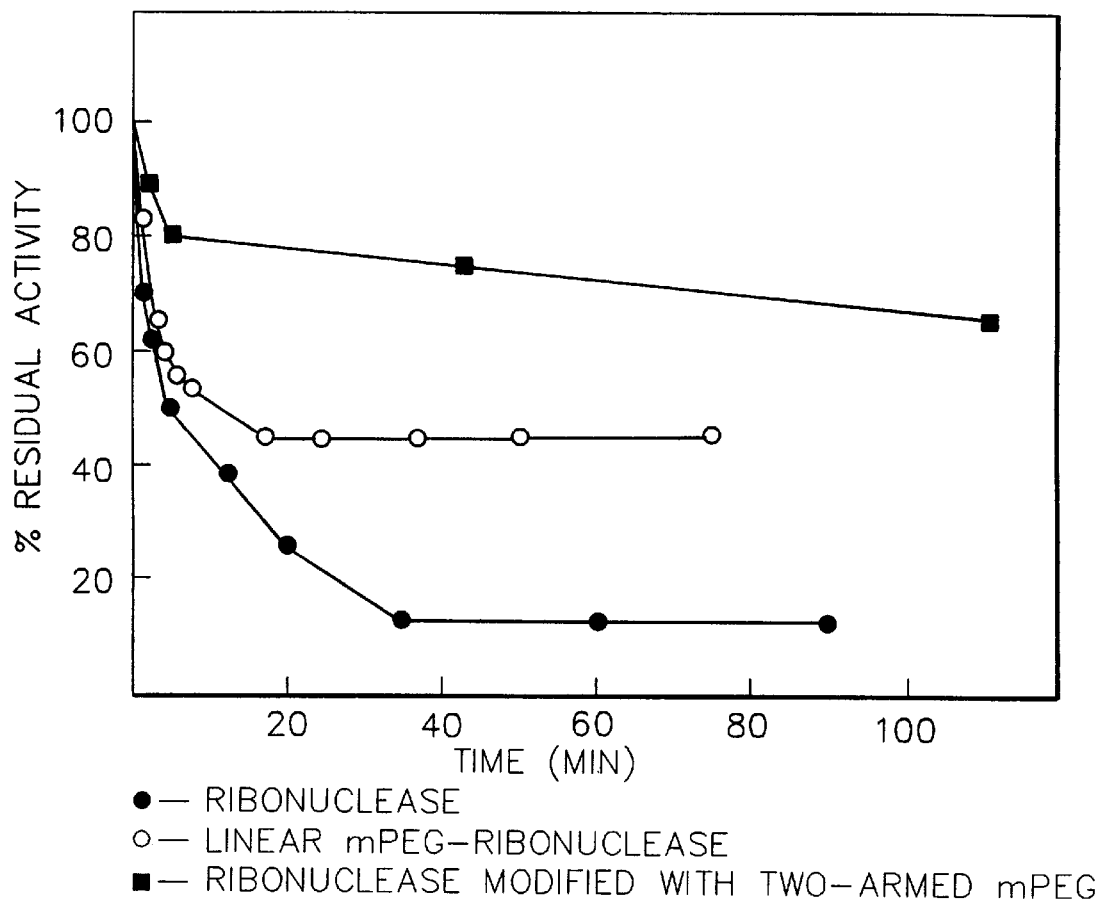

For native ribonuclease and its linear and two-armed mPEG conjugates, 0.57 mg protein was digested at room temperature with 2.85 mg of pronase, or 5.7 mg of elastase, or with 0.57 mg of subtilisin in a total volume of 1 ml. Ribonuclease with 50% and 55% of the amino groups modified with linear mPEG and two-armed mPEG, respectively, was studied for stability to proteolytic digestion by pronase (FIG. 1(a)), elastase (FIG. 1(b)) and subtilisin (FIG. 1(c)). Polymer modification greatly increases the stability to digestion by all three proteolytic enzymes, but the protection offered by two-armed mPEG is much more effective as compared to linear mPEG.

Figure 3A:
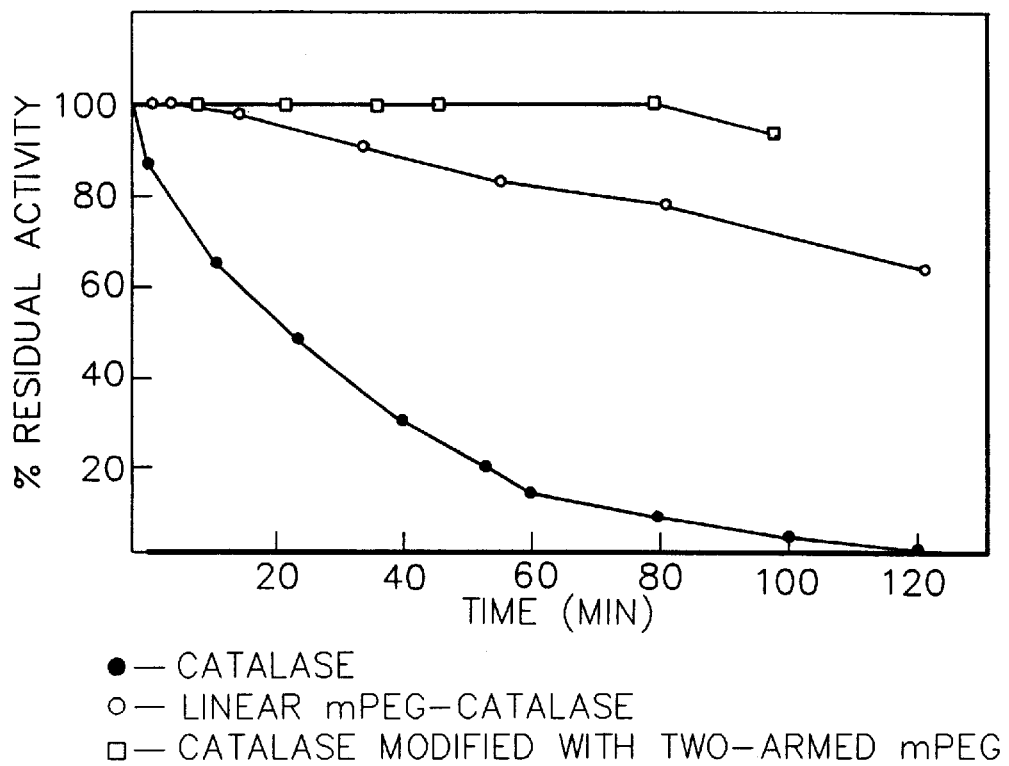
FIGS. 3(a) and 3(b) illustrate the time course of digestion for catalase (●), linear mPEG-modified catalase (○), and catalase modified with a multi-armed mPEG of the invention (■) as assessed by enzyme activity upon incubation with pronase (FIG. 3(a)) and trypsin (FIG. 3(b)).
Figure 3B:
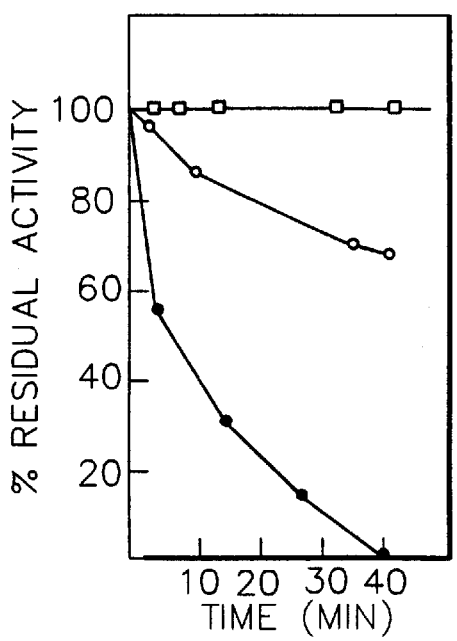

For native and linear and two-armed mPEG-modified catalase, 0.58 mg of protein were digested at room temperature with 0.58 mg of trypsin or 3.48 mg of pronase in a total volume of 1 ml. Catalase was modified with linear mPEG and two-armed mPEG to obtain 43% and 38% modification of protein amino groups, respectively. Proteolytic stability was much greater for the two-armed mPEG derivative than for the monosubstituted mPEG derivative, particularly toward pronase (FIG. 3(a)) and trypsin (FIG. 3(b)), where no digestion took place.

Autolysis of trypsin and its linear and two-armed mPEG derivatives at 37° C. was evaluated by esterolytic activity of protein solutions at 25 mg/ml of TAME. Trypsin modification was at the level of 50% and 57% of amino groups with linear mPEG and two-armed mPEG, respectively. Modification with linear mPEG and two-armed mPEG reduced proteolytic activity of trypsin towards casein, a high molecular weight substrate: activity relative to the native enzyme was found, after 20 minutes incubation, to be 64% for the linear mPEG and protein conjugate and only 35%. for the two-armed mPEG conjugate. In agreement with these results, the trypsin autolysis rate (i.e., the rate at which trypsin digests trypsin), evaluated by enzyme esterolytic activity, was totally prevented in two-armed mPEG-trypsin but only reduced in the linear mPEG-trypsin conjugate. To prevent autolysis with linear mPEG, modification of 78% of the available protein amino groups was required.

Figure 5:
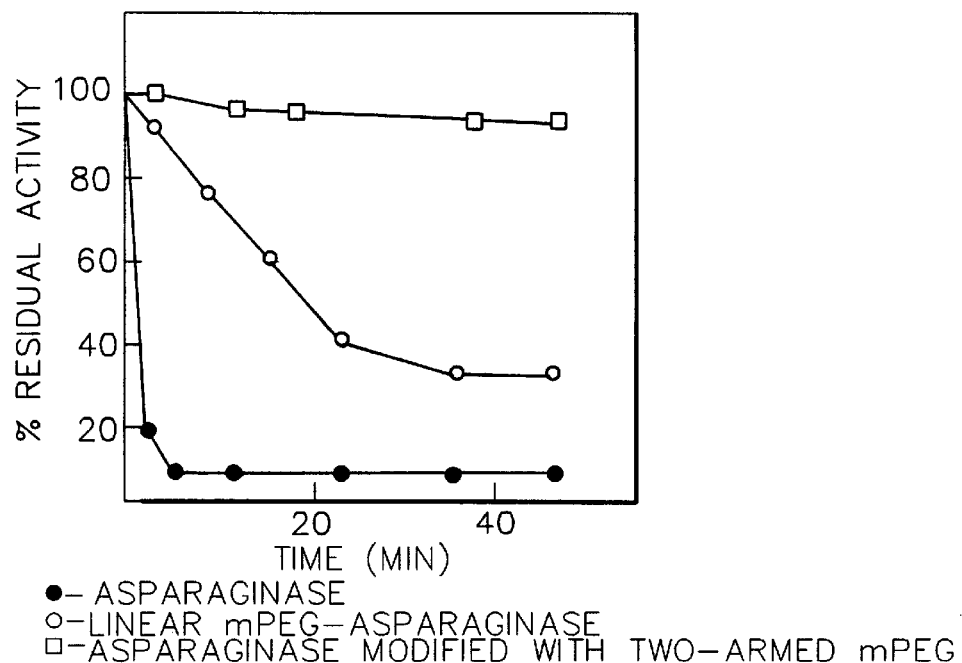
FIG. 5 illustrates the time course of digestion of asparaginase (●), linear mPEG-modified asparaginase (○), and asparaginase modified with a multi-armed mPEG of the invention (■) as assessed by enzyme activity assay upon trypsin incubation.
Figure 6:
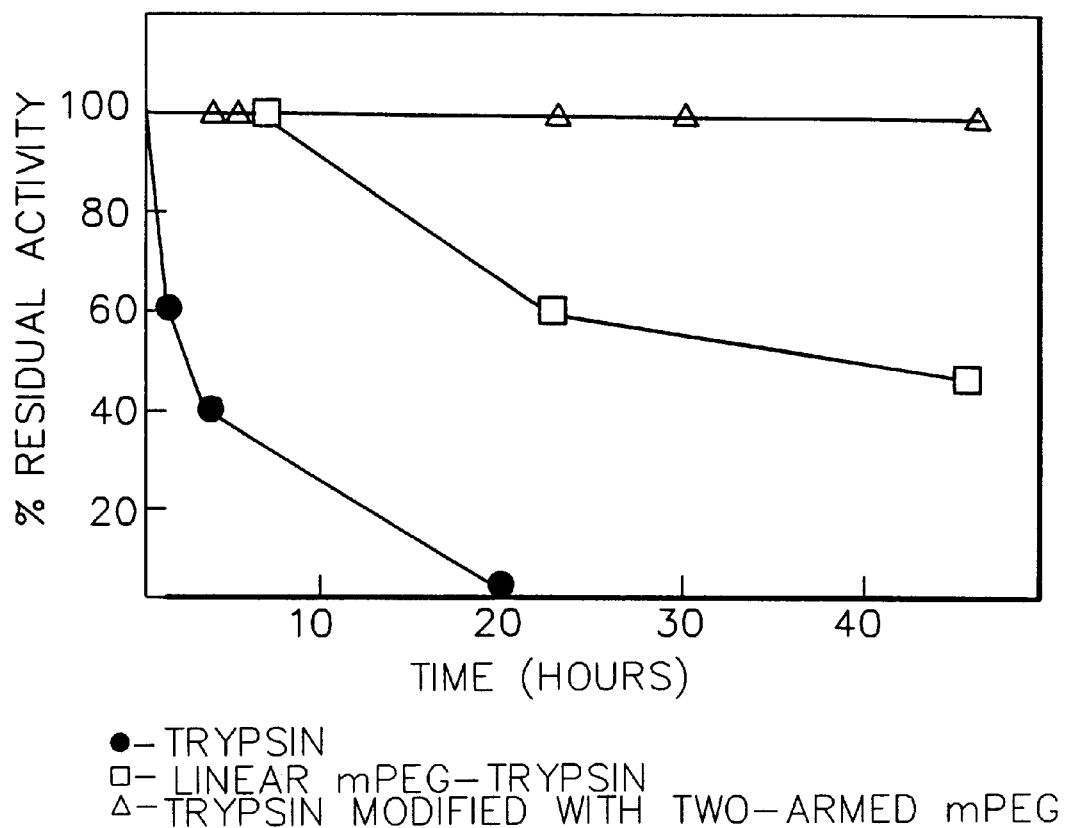
FIG. 6 illustrates the time course of autolysis of trypsin (●), linear mPEG-modified trypsin (■), and trypsin modified with a multi-armed mPEG of the invention (▲) evaluated as residual activity towards TAME (alpha N-p-tosyl-arginine methyl ester).

For native and linear mPEG- and two-armed mPEG-modified asparaginase, 2.5 μg were digested at 37° C. with 0.75 mg of trypsin in a total volume of 1 ml. Asparaginase with 53% and 40% modified protein amino groups was obtained by coupling with linear mPEG and two-armed mPEG, respectively. Modification with two-armed mPEG had an impressive influence on stability towards proteolytic enzyme. Increased protection was achieved at a lower extent of modification with respect to the derivative obtained with the two-armed polymer (FIG. 5).

These data clearly show that two-armed mPEG coupling is much more effective than conventional linear mPEG coupling in providing a protein with protection against proteolysis. While not wishing to be bound by theory, it is believed that the two-armed mPEG, having two polymer chains bound to the same site, presents increased hindrance to approaching macromolecules in comparison to linear mPEG.

C. Reduction of Protein Antigenicity. Protein can provoke an immune response when injected into the bloodstream. Reduction of protein immunogenicity by modification with linear and two-armed mPEG was determined and compared for the enzyme superoxidedismutase ("SOD").

Anti-SOD antibodies were obtained from rabbit and purified by affinity chromatography. The antigens (SOD, linear mPEG-SOD, and two-armed mPEG-SOD) were labelled with tritiated succinimidyl propionate to facilitate tracing. Reaction of antigen and antibody were evaluated by radioactive counting. In a 500 μL sample, the antigen (in the range of 0–3 μg) was incubated with 2.5 μg of antibody. The results show the practical disappearance of antibody recognition for two-armed mPEG-SOD, while an appreciable antibody-antigen complex was formed for linear mPEG-SOD and native SOD.

D. Blood Clearance Times. Increased blood circulation half lives are of enormous pharmaceutical importance. The degree to which mPEG conjugation of proteins reduces kidney clearance of proteins from the blood was determined and compared for free protein, protein modified by attachment of conventional, linear activated mPEG, and protein modified by attachment of the activated two-armed mPEG of the invention. Two proteins were used. These experiments were conducted by assaying blood of mice for the presence of the protein.

For linear mPEG-uricase and two-armed mPEG-uricase, with 40% modification of lysine groups, the half life for blood clearance was 200 and 350 minutes, respectively. For unmodified uricase the result was 50 minutes.

For asparaginase, with 53% modification with mPEG and 40% modification with two armed mPEG, the half lives for blood clearance were 1300 and 2600 minutes, respectively. For unmodified asparaginase the result was 27 minutes.

E. Thermal Stability of Free and Conjugated Enzymes. Thermal stability of native ribonuclease, catalase and asparaginase and their linear mPEG and two-armed mPEG conjugates was evaluated in 0.5M phosphate buffer pH 7.0 at 1 mg/ml, 9 μg/ml and 0.2 mg/ml respectively. The samples were incubated at the specified temperatures for 15 min., 10 min., and 15 min, respectively, cooled to room temperature and assayed spectrophotometrically for activity.

Figure 2A:
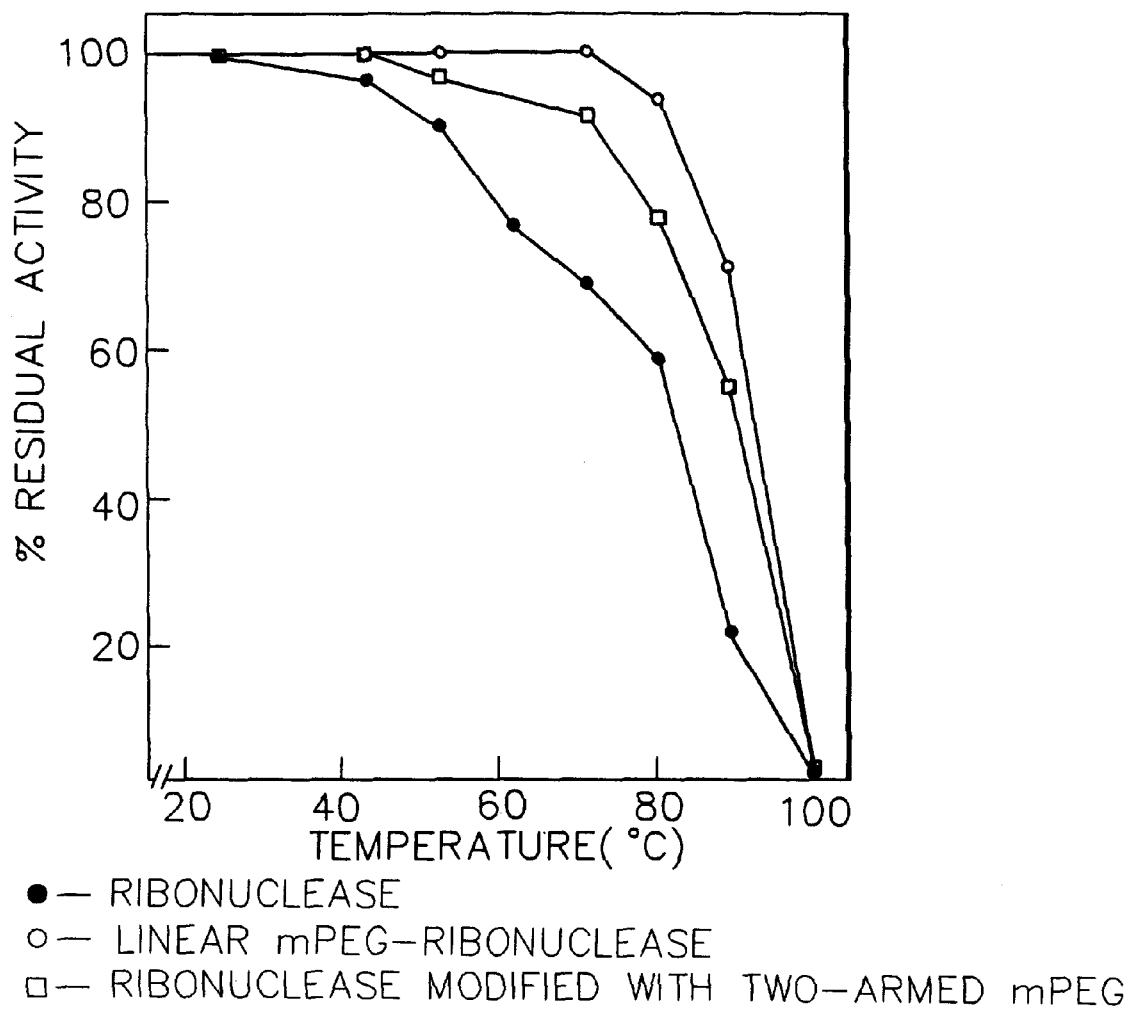
FIGS. 2(a) and 2(b) illustrate stability toward heat (FIG. 2(a)) and pH (FIG. 2(b)) of ribonuclease (●), linear mPEG-modified ribonuclease (○), and ribonuclease modified with a multi-armed mPEG of the invention (□).

Increased thermostability was found for the modified forms of ribonuclease, as shown in FIG. 2, at pH 7.0, after 15 min. incubation at different temperatures, but no significant difference between the two polymers was observed. Data for catalase, not reported here, showed that modification did not influence catalase thermostability. A limited increase in thermal stability of linear and two-armed mPEG-modified asparaginase was also noted, but is not reported.

F. pH Stability of the Free and Conjugated Enzymes. Unmodified and polymer-modified enzymes were incubated for 20 hrs in the following buffers: sodium acetate 0.05M at a pH of from 4.0 to 6.0, sodium phosphate 0.05M at pH 7.0 and sodium borate 0.05M at a pH of from 8.0 to 11. The enzyme concentrations were 1 mg/ml, 9 μg/ml, 5 μg/ml for ribonuclease, catalase, and asparaginase respectively. The stability to incubation at various pH was evaluated on the basis of enzyme activity.

Figure 2B:
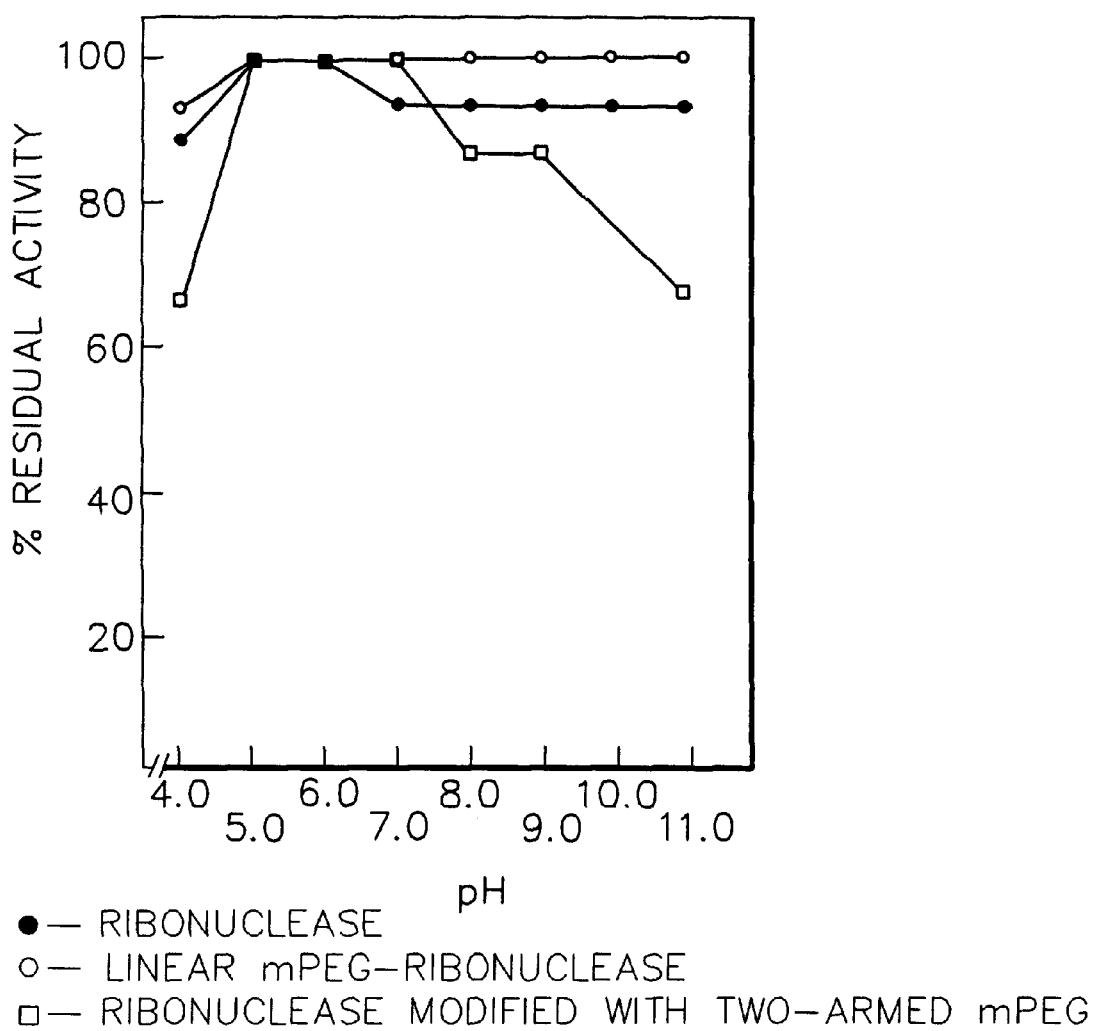
Figure 4:
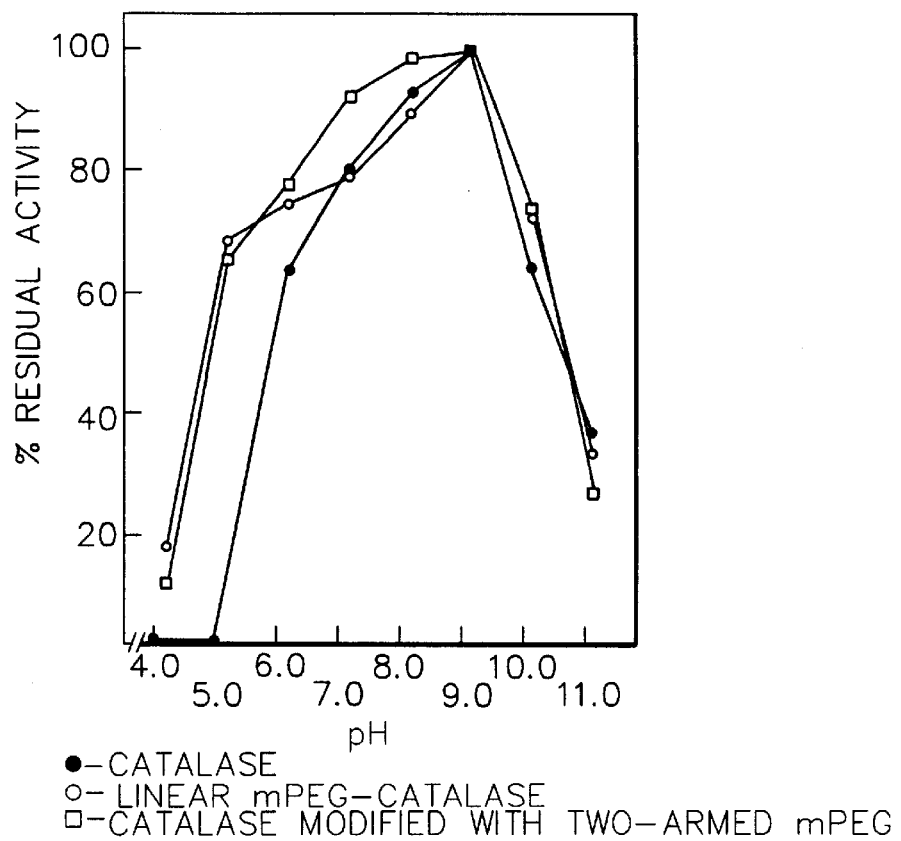
FIG. 4 illustrates the stability of catalase (●), linear mPEG-modified catalase (□), and catalase modified with a multi-armed mPEG of the invention (○) for 20 hours incubation at the indicated pH values.

As shown in FIG. 2b, a decrease in pH stability at acid and alkline pH values was found for the linear and two-armed mPEG-modified ribonuclease forms as compared to the native enzyme. As shown in FIG. 4, stability of the linear mPEG and two-armed mPEG conjugates with catalase was improved for incubation at low pH as compared to native catalase. However, the two-armed mPEG and linear mPEG conjugates showed equivalent pH stability. A limited increase in pH stability at acid and alkaline pH values was noted for linear and two-armed mPEG-modified asparaginase as compared to the native enzyme.

It should be recognized that there are thousands of proteins and enzymes that can be usefully modified by attachment to the polymer derivatives of the invention. Proteins and enzymes can be derived from animal sources, humans, microorganisms, and plants and can be produced by genetic engineering or synthesis. Representatives include: cytokines such as various interferons (e.g. interferon-α, interferon-β, interferon-γ), interleukin-2 and interleukin-3), hormones such as insulin, growth hormone-releasing factor (GRF), calcitonin, calcitonin gene related peptide (CGRP), atrial natriuretic peptide (ANP), vasopressin, corticortropin-releasing factor (CRF), vasoactive intestinal peptide (VIP), secretin, α-melanocyte-stimulating hormone (α-MSH), adrenocorticotropic hormone (ACTH), cholecystokinin (CCK), glucagon, parathyroid hormone (PTH), somatostatin, endothelin, substance P, dynorphin, oxytocin and growth hormone-releasing peptide, tumor necrosis factor binding protein, growth factors such as growth hormone (GH), insulin-like growth factor (IGF-I, IGF-II), β-nerve growth factor (β-NGF), basic fibroblast growth factor (bFGF), transforming growth factor, erythropoietin, granulocyte colony-stimulating factor (G-CSF), granulocyte macrophage colony-stimulating factor (GM-CSF), platelet-derived growth factor (PDGF) and epidermal growth factor (EGF), enzymes such as tissue plasminogen activator (t-PA), elastase, superoxide dismutase (SOD), bilirubin oxydase, catalase, uricase and asparaginase, other proteins such as ubiquitin, islet activating protein (IAP), serum thymic factor (STF), peptide-T and trypsin inhibitor, and derivatives thereof. In addition to protein modification, the two-armed polymer derivative of the invention has a variety of related applications. Small molecules attached to two-armed activated mPEG derivatives of the invention can be expected to show enhanced solubility in either aqueous or organic solvents. Lipids and liposomes attached to the derivative of the invention can be expected to show long blood circulation lifetimes. Other particles than lipids and surfaces having the derivative of the invention attached can be expected to show nonfouling characteristics and to be useful as biomaterials having increased blood compatibility and avoidance of protein adsorption. Polymer-ligand conjugates can be prepared that are useful in two phase affinity partitioning. The polymers of the invention could be attached to various forms of drugs to produce prodrugs. Small drugs having the multisubstituted derivative attached can be expected to show altered solubility, clearance time, targeting, and other properties.

The invention claimed herein has been described with respect to particular exemplified embodiments. However, the foregoing description is not intended to limit the invention to the exemplified embodiments, and the skilled artisan should recognize that variations can be made within the scope and spirit of the invention as described in the foregoing specification. The invention includes all alternatives, modifications, and equivalents that may be included within the true spirit and scope of the invention as defined by the appended claims.

What is claimed is:

1. An essentially pure water soluble polymer having a moiety located along the polymer backbone, which moiety comprises a single ionizable reactive group, wherein said polymer is represented by the structure:

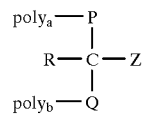

wherein C is carbon; wherein R is a nonreactive moiety; wherein Z is said moiety comprising a single ionizable reactive group; wherein poly$_a$ and poly$_b$ are nonpeptidic and nonreactive polymeric arms that may be the game or different; wherein P and Q are nonreactive linkage fragments that may be the same or different and join polymeric arms poly$_a$ and poly$_b$, respectively, to C in the absence of aromatic rings and ester groups in said fragments, and wherein said polymer is recovered in essentially pure form by ion exchange chromatography.

2. The polymer of claim 1 wherein said single ionizable reactive group is a carboxyl group.

3. The polymer of claim 1 wherein said recovered polymer is activated for reaction with nucleophilic groups.

4. A conjugate of the polymer of claim 3 and a nucleophilic group.

5. The polymer of claim 1 wherein said nonpeptidic and nonreactive polymeric arms are selected from the group consisting of poly(alkylene oxides), poly(oxyethylated polyols), poly(oxyethylated glucose), and copolymers, terpolymers, and mixtures thereof.

6. The polymer of claim 1 wherein said nonpeptidic and nonreactive polymeric arms are selected from the group consisting of polyethylene glycol), poly(vinyl alcohol), polypropylene glycol), poly(oxyethylated glycerol), poly (oxyethylated sorbitol), poly(oxyethylated glucose), poly (oxazoline), poly(acryloylmorpholine), poly (vinylpyrrolidone), and copolymers, terpolymers, and mixtures thereof.

7. The polymer of claim 1 wherein said nonpeptidic and nonreactive polymeric arms are polyethylene glycol arms, each said arm having a molecular weight of from about 50 to 50,000.

8. The polymer of claim 1 wherein said nonpeptidic nonreactive polymeric arms are polyethylene glycol arms and said polymer has a molecular weight of from about 40,000 to 100,000.

9. The polymer of claim 1 wherein said linkage fragments P and Q comprise moieties selected from the group consisting of amide, amine, ether, carbamate, thiourea, urea, thiocarbamate, thiocarbonate, thioether, thioester, and dithiocarbamate moieties.

10. The polymer of claim 1 wherein said polymer has a structure selected from the group consisting of:

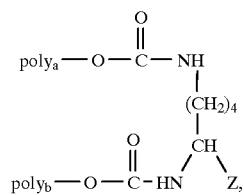

(1)

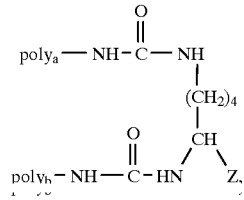

(2)

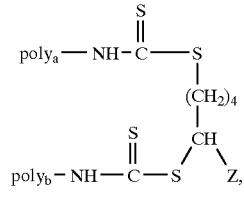

(3)

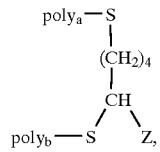

(4)

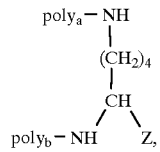

(5)

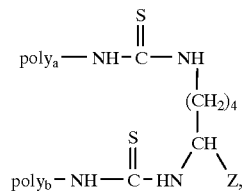

(6)

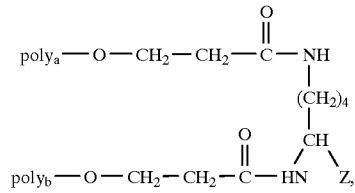

(7)

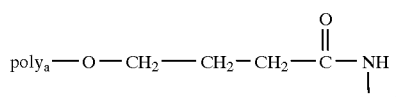
(8)

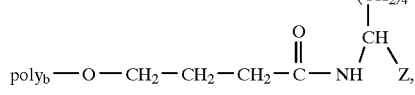
(9)

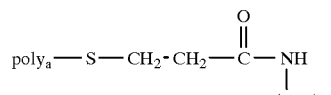
(10)

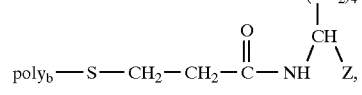
(11)

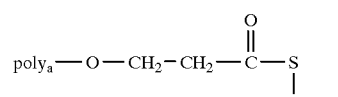
(12)

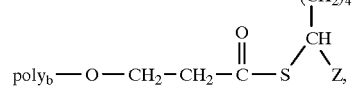
(13)

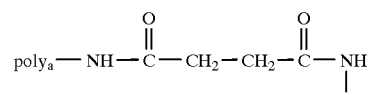

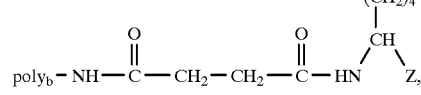

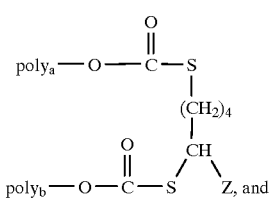

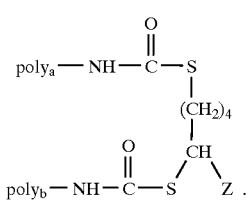

11. The polymer of claim 3 activated as trifluoroethylsulfonyl, isocyanate, isothiocyanate, active esters, active carbonates, aldehyde, vinylsulfone, maleimide, iodoacetamide, and iminoesters.

12. The polymer of claim 11 wherein said active ester is N-hydroxylsuccinimidyl ester and wherein said active carbonates are selected from the group consisting of N-hydroxylsuccinimidyl carbonate, p-nitrophenylcarbonate, and trichlorophenylcarbonate.

13. The polymer of claim 3 wherein said nucleophilic moieties are selected from the group consisting of amino, thiol, and hydroxyl moieties.

14. The conjugate of claim 4 wherein a biologically active molecule comprise said nucleophilic group.

15. The conjugate of claim 14 wherein said biologically active molecule is selected from the group consisting of enzymes, peptides, polypeptides, nucleotides, polynucleotides, and lipids.

16. The conjugate of claim 4 wherein a solid surface comprises said nucleophilic group.

17. The conjugate of claim 16 wherein said solid surface is a liposome.

18. An essentially pure water soluble polymer represented by the structure:

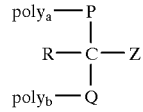

wherein C is carbon; wherein Z comprises a single ionizable reactive group; wherein R comprises -M-$poly_d$; wherein $poly_a$, $poly_b$, and $poly_d$ are nonpeptidic and nonreactive polymeric arms that may be the same or different; wherein P, Q, and M are nonreactive linkage fragments that may be the same or different and join polymeric arms $poly_a$, $poly_b$, and $poly_d$, respectively, to C in the absence of aromatic rings and ester groups in said linkage fragments, and wherein said polymer is recovered in essentially pure form by ion exchange chromatography.

19. An essentially pure water soluble polymer having a molecular weight of from about 40,000 to 100,000 wherein said polymer is represented by the structure:

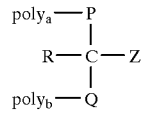

wherein C is carbon; wherein R is a nonreactive moiety; wherein Z comprises a single carboxyl moiety, —COOH; wherein $poly_a$ and $poly_b$ are polyethylene glycol arms that may be of the same or different molecular weight; wherein P and Q are nonreactive linkage fragments that may be the same or different and join polymeric arms $poly_a$ and $poly_b$, respectively, to C in the absence of aromatic rings and carbonate ester moieties in said fragments, and wherein said polymer in recovered in essentially sure form by ion exchange chromatography.

20. An essentially pure monomethoxy poly(ethylene glycol) disubstituted lysine represented by the following structure:

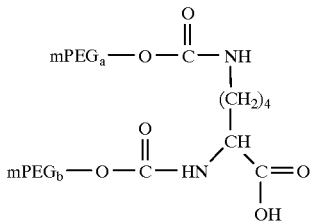

wherein $mPEG_a$ and $mPEG_b$ are monomethoxypoly (ethylene glycols) having the structure CH—($CH_2CH_2O$) $_nCH_2CH_2$—, wherein n equals from 1 to about one thousand one hundred fifty (1,150), wherein n may be the same or different for $mPEG_a$ and $mPEG_b$, and wherein said disubstituted lysine is recovered in essentially pure form by ion exchange chromatography.

21. The monomethoxy polyethylene glycol) disubstituted lysine of claim 20 activated for reaction with nucleophilic moieties.

22. A conjugate of the activated monomethoxy poly (ethylene glycol) disubstituted lysine of claim 21 and a nucleophilic moiety.

23. The monomethoxy poly(ethylene glycol) disubstituted lysine of claim 21 activated as the succinimidyl ester.

24. A conjugate of a biologically active molecule and the monomethoxy poly(ethylene glycol) disubstituted lysine of claim 23 activated as the succinimidyl ester.

25. A method of synthesizing a water soluble, branched polymer having a single ionizable reactive group, which ionizable reactive group is located along the polymer backbone, said method comprising the steps of:
a) reacting two or more nonpeptidic and monofunctional polymers of the structure poly-W, wherein W is an active moiety located at the terminus of the polymer that provides the monofunctionality for the polymer, with a linger molecule having two or more active sites with which W is reactive and forming linkages therewith to create a branched polymer, wherein said linker molecule and said linkages do not comprise aromatic rings and ester groups and wherein the linker molecule further comprises a single reactive group with which active moiety —W is not reactive and that provides the single ionizable reactive group on the branched polymer backbone; and
b) recovering the branched polymer in essentially pure form by ion exchange chromatography.

26. The method of claim 25 wherein said single ionizable reactive group is carboxyl.

27. The method of claim 25 wherein the linkages between the linker molecule and monofunctional polymers poly-W are formed in a single step.

28. The method of claim 25 wherein a first linkage formed between the linker molecule and the monofunctional polymer poly-W in a first step, and wherein a second linkage of the linker molecule and poly-W is formed in a second step.

29. The method of claim 28 wherein the first step occurs in aqueous buffer and the second step occurs in a nonaqueous medium.

30. The method of claim 25 wherein the active moiety W is an electrophilic moiety selected from the group consisting of trifluoroethylsulfonate, isocyanate, isothiocyanate, active esters, active carbonates, aldehyde, vinylsulfone, maleimide, iodoacetamide, and iminoesters.

31. The method of claim 30 wherein the active ester is N-hydroxylsuccinimidyl ester and the active carbonates are selected from the group consisting of N-hydroxylsuccinimidyl carbonate, p-nitrophenylcarbonate, and trichlorophenylcarbonate.

32. The method of claim 25 wherein the active moiety W is a nucleophilic moiety selected from the group consisting of amino, thiol, and hydroxyl moieties.

33. The method of claim 32 wherein the active sites on the linker moiety are electrophilic moieties selected from the group consisting of trifluoroethylsulfonate, isocyanate, isothiocyanate, active esters, active carbonates, aldehyde, vinylsulfone, maleimide, iodoacetamide, and iminoesters.

34. The method of claim 33 wherein the active ester is N-hydroxylsuccinimidyl ester and the active carbonates are selected from the group consisting of N-hydroxylsuccinimidyl carbonate, p-nitrophenylcarbonate, and trichlorophenylcarbonate.

35. The method of claim 25 wherein the linkages are selected from the group consisting of amide, amine, ether, carbamate, thiourea, urea, thiocarbamate, thiocarbonate, thioether, thioester, and dithiocarbamate linkages.

36. The method of claim 25 further comprising the step of activating the single ionizable reactive group on said polymer backbone for reaction with nucleophilic moieties.

37. The method of claim 36 wherein the group activated for reaction with nucleophilic moieties is an electrophilic moiety that is reactive with nucleophilic moieties selected from the group consisting of amino, thiol, and hydroxyl moieties.

38. The method of claim 37 wherein the electrophilic moiety is selected from the group consisting of trifluoroethylsulfonate, isocyanate, isothiocyanate, active esters, active carbonates, aldehyde, vinylsulfone, maleimide, iodoacetamide, and iminoesters.

39. A method for forming monofunctional monomethoxy-poly(ethylene glycol) disubstituted lysine comprising carrying out steps to perform the following rejection:

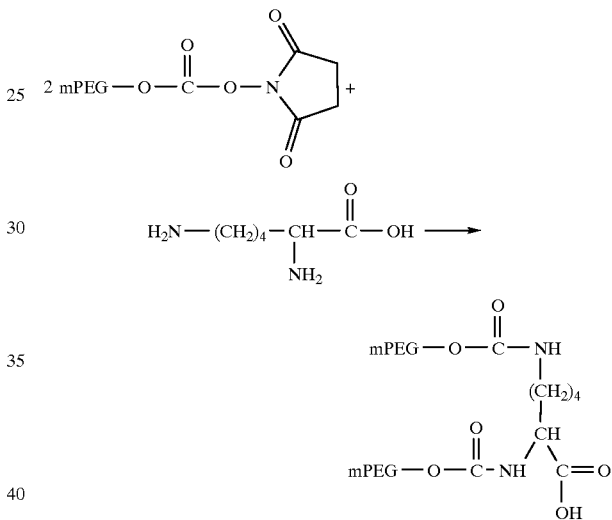

and recovering the disubstituted lysine in essentially pure form by ion exchange chromatography.

40. The method of claim 39 wherein the reaction takes place in water at a pH of about 8.0.

41. The method of claim 40 further comprising carrying out steps to perform the following reactions:

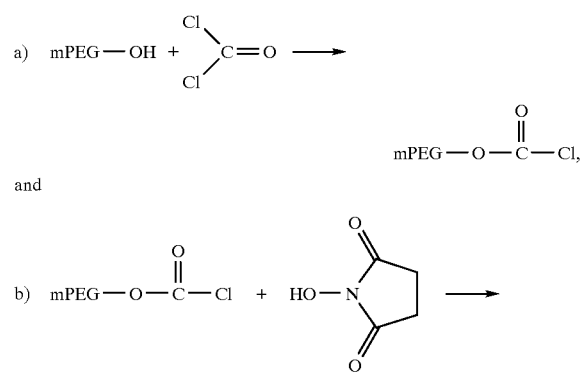

-continued

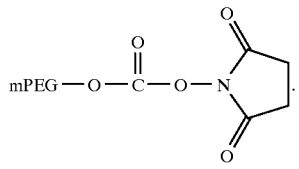

42. The method of claim 41 wherein reactions a) and b) take place in methylene chloride.

43. The method of claim 39 further comprising the steps of activating the carboxyl moiety of the recovered disubstituted lysine for reaction with nucleophilic moieties and then reacting the activated carboxyl moiety with a nucleophilic moiety to join the disubstituted lysine to the nucleophilic moiety.

44. A method for forming a monofunctional monomethoxy-poly(ethylene glycol) disubstituted lysine comprising carrying out steps to perform the following reactions:

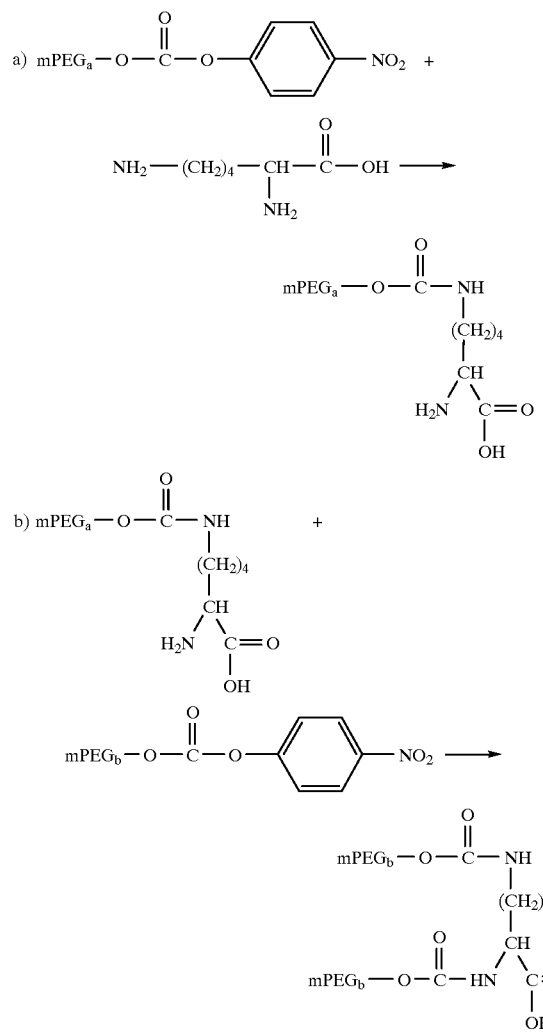

and recovering the disubstituted lysine in essentially pure form by ion exchange chromatography.

45. The method of claim 44 further comprising the steps of activating the carboxyl moiety of the recovered disubstituted lysine for reaction with nucleophilic moieties and then reacting the activated carboxyl moiety with a nucleophilic moiety to join the disubstituted lysine to the nucleophilic moiety.

46. The method of claim 44 wherein reaction (a) takes place in aqueous buffer.

47. The method of claim 44 wherein reaction (b) takes place in methylene chloride.

48. A method of preparing monomethoxy poly(ethylene glycol)-disubstituted lysine activated as the succinimidyl ester, comprising carrying out steps to react the recovered disubstituted lysine produced by the method of claim 39 or claim 44 an follows:

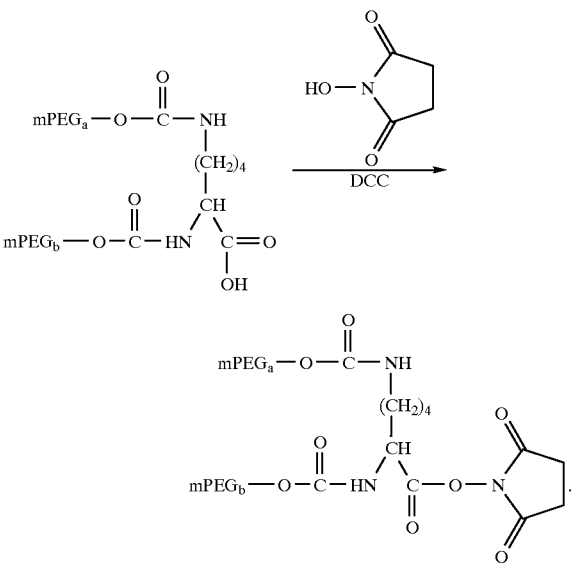

49. A polymeric derivative having a structure selected from the group consisting of:

(1)

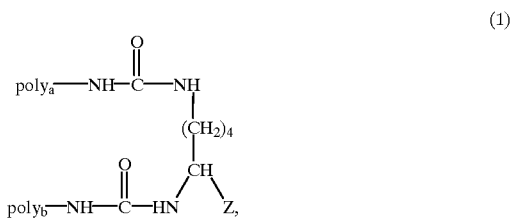

(2)

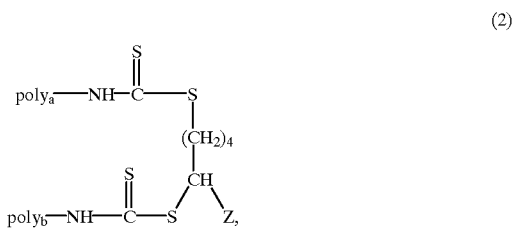

(3)

(4) 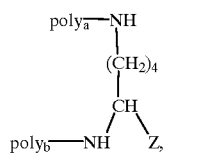

(5) 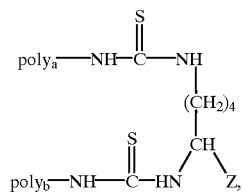

(6) 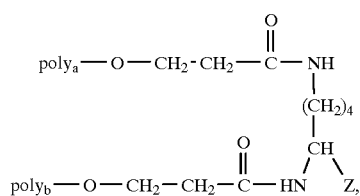

(7) 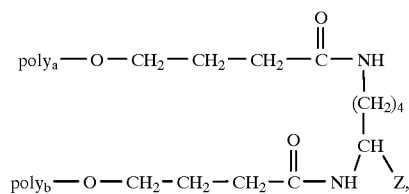

(8) 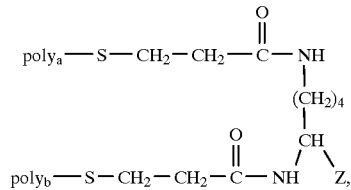

(9) 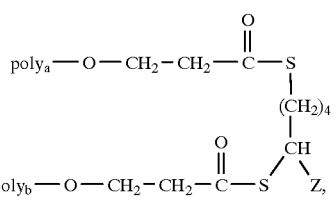

(10)  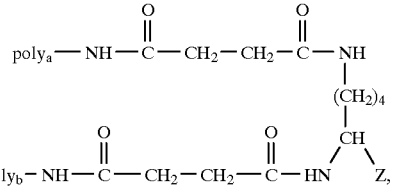

(11) 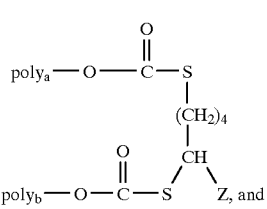, and

(12) 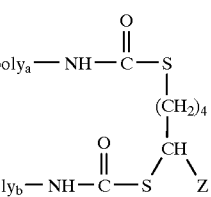

wherein $poly_a$ and $poly_b$ are nonpeptidic and nonreactive polymeric arms that may be the same or different; and wherein Z comprises a moiety selected from the group consisting of moieties having a single site reactive toward nucleophilic moieties, sites that can be converted to sites reactive toward nucleophilic moieties, and the reaction product of a nucleophilic moiety and moieties having a single site reactive toward nucleophilic moieties.

* * * * *

UNITED STATES PATENT AND TRADEMARK OFFICE
CERTIFICATE OF CORRECTION

PATENT NO. : 5,932,462

DATED : August 3, 1999

INVENTOR(S) : Harris et al.

It is certified that error appears in the above-identified patent and that said Letters Patent is hereby corrected as shown below:

On the title page, item [54] and Column 1, line 1, in the title, after "MONOFUNCTIONAL" cancel the comma (,).

On the title page, [75] Inventors, in the second through fourth inventors' addresses, "Padua" should read --Padova--.

On the title page, [56] References Cited, U.S. PATENT DOCUMENTS, line 4, "Ekuiuribe" should read --Ekwuribe--.

UNITED STATES PATENT AND TRADEMARK OFFICE
CERTIFICATE OF CORRECTION

PATENT NO. : 5,932,462
DATED : August 3, 1999
INVENTOR(S) : Harris et al.

Page 2 of 4

It is certified that error appears in the above-identified patent and that said Letters Patent is hereby corrected as shown below:

Columns 5 - 6, before the plus marks (+), in step 2, insert --(A)--; in step 3, insert --(B)--; in step 4, insert --(C)-- as follows:

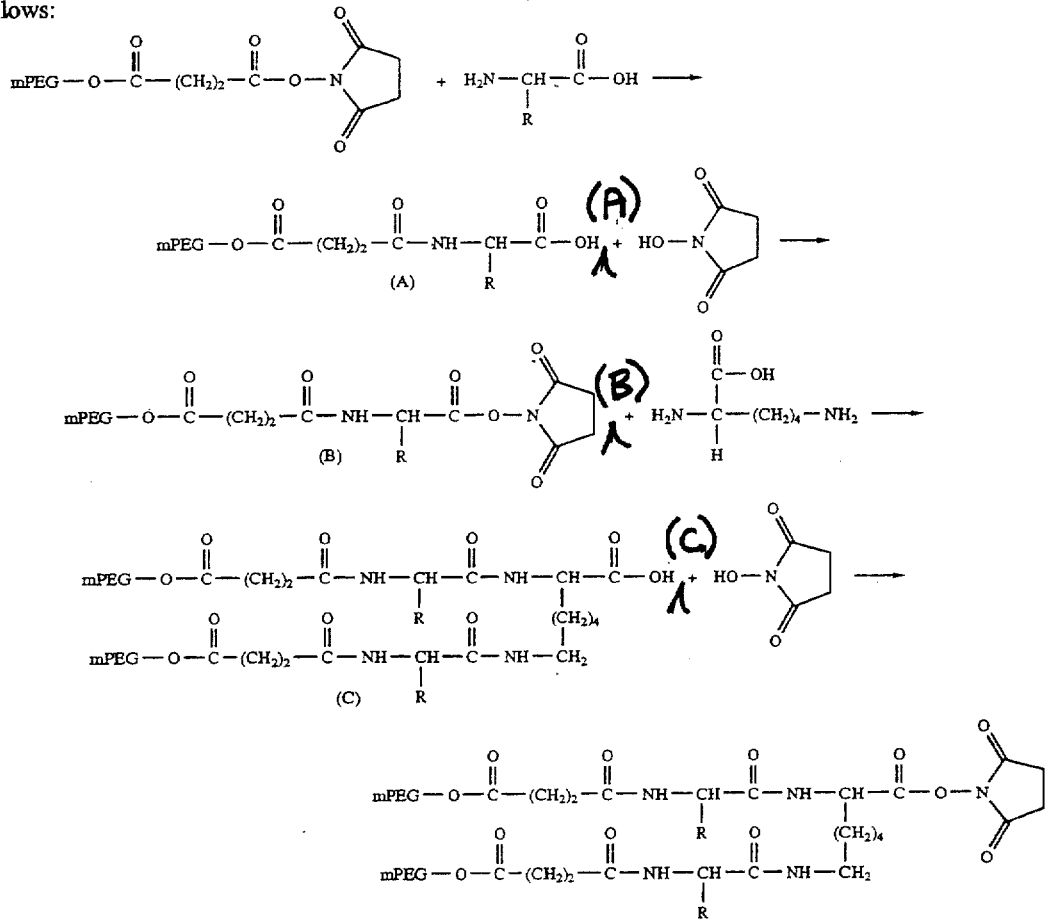

UNITED STATES PATENT AND TRADEMARK OFFICE
CERTIFICATE OF CORRECTION

PATENT NO. : 5,932,462

DATED : August 3, 1999

INVENTOR(S) : Harris et al.

It is certified that error appears in the above-identified patent and that said Letters Patent is hereby corrected as shown below:

Column 11, line 60, "linkage-joining" should read --linkage joining--.

Column 17, line 48, "90w" should read --90%--.

Column 22, line 36, "Thiocarbonate" should read --Thiocarbamate--.

Column 29, line 8, before "The" insert a period (.); line 17, after "95%" cancel the period (.).

Column 34, line 5, "Tryosinogen" should read --Trypsinogen--; line 6, "tryosin" should read --trypsin--; line 66, after "35%" cancel the period (.).

Column 37, line 32, "game" should read --same--; line 52, "polyethylene glycol)" should read --poly(ethylene glycol)--; line 53, "polypropylene glycol)" should read --poly(propylene glycol)--; line 62, after "nonpeptidic" insert --and--.

Column 39, line 55, "trifluoroethylsulfonyl" should read --trifluoroethylsulfonate--; line 67, "comprise" should read --comprises--.

Column 40, line 45, "sure" should read --pure--; line 62, $CH-(CH_2CH_2O)$ should read --$CH_3-(CH_2CH_2O)$--.

UNITED STATES PATENT AND TRADEMARK OFFICE
CERTIFICATE OF CORRECTION

PATENT NO. : 5,932,462
DATED : August 3, 1999
INVENTOR(S) : Harris et al.

It is certified that error appears in the above-identified patent and that said Letters Patent is hereby corrected as shown below:

Column 41, line 1, "polyethylene glycol)" should read --poly(ethylene glycol)--; line 20, "linger" should read --linker--; line 36, after "linkage" insert --is--.

Column 42, line 20, "rejection" should read --reaction--.

Column 43, line 54, "mPEG$_b$" should read --mPEG$_a$--.

Column 44, line 12, "an" should read --as--.

Signed and Sealed this

Twelfth Day of September, 2000

Attest:

Q. TODD DICKINSON

*Attesting Officer*          *Director of Patents and Trademarks*